US010258976B2

(12) United States Patent
Fontaine et al.

(10) Patent No.: US 10,258,976 B2
(45) Date of Patent: Apr. 16, 2019

(54) PRECATALYSTS AND PROCESS FOR THE METAL-FREE FUNCTIONALIZATION OF SP$^2$ CARBONS USING THE SAME

(71) Applicant: UNIVERSITÉ LAVAL, Québec (CA)

(72) Inventors: Frédéric-Georges Fontaine, Québec (CA); Marc-André Légaré, Québec (CA); Étienne Rochette, St-Augustin-de-Desmaures (CA)

(73) Assignee: UNIVERSITÉ LAVAL, Quebec (CA)

( * ) Notice: Subject to any disclaimer, the term of this patent is extended or adjusted under 35 U.S.C. 154(b) by 0 days.

(21) Appl. No.: 15/780,942

(22) PCT Filed: Dec. 15, 2016

(86) PCT No.: PCT/CA2016/000318
§ 371 (c)(1),
(2) Date: Jun. 1, 2018

(87) PCT Pub. No.: WO2017/100904
PCT Pub. Date: Jun. 22, 2017

(65) Prior Publication Data
US 2018/0280950 A1 Oct. 4, 2018

Related U.S. Application Data

(60) Provisional application No. 62/267,637, filed on Dec. 15, 2015.

(51) Int. Cl.
| | | |
|---|---|---|
| *C07F 5/02* | (2006.01) | |
| *B01J 31/02* | (2006.01) | |
| *B01J 31/14* | (2006.01) | |
| *B01J 31/22* | (2006.01) | |

(52) U.S. Cl.
CPC ............. *B01J 31/146* (2013.01); *B01J 31/22* (2013.01); *C07F 5/02* (2013.01); *B01J 31/0231* (2013.01); *B01J 31/0239* (2013.01); *B01J 31/0271* (2013.01); *B01J 2231/4277* (2013.01)

(58) Field of Classification Search
USPC .......................................................... 546/13
See application file for complete search history.

(56) References Cited

U.S. PATENT DOCUMENTS

| | | | | |
|---|---|---|---|---|
| 9,856,194 B2* | 1/2018 | Fontaine | ............... | B01J 31/0267 |
| 2007/0178370 A1 | 8/2007 | Amine et al. | | |
| 2014/0350303 A1* | 11/2014 | Fontaine | ............... | B01J 31/0267 568/2 |
| 2018/0094001 A1* | 4/2018 | Fontaine | ................. | C07B 47/00 |

FOREIGN PATENT DOCUMENTS

| | | |
|---|---|---|
| CA | 2903281 | 9/2014 |
| WO | WO 2016/168914 | 10/1916 |
| WO | WO-2004113351 A2 * | 12/2004 ............... C07F 5/02 |
| WO | WO 2008/125911 | 10/2008 |
| WO | WO 2013/177708 | 12/2013 |

OTHER PUBLICATIONS

Chiu; J. Am. Chem. Soc., 2006, 128, 14248-14249. (Year: 2006).*
Coghlan; Journal of Organometallic Chemistry 2005, 690, 4784-4793. (Year: 2005).*
Couch; Chem. Eur. J. 2014, 20, 8283-8287. (Year: 2014).*
Giles; Journal of Organometallic Chemistry 2003, 680, 257-262. (Year: 2003).*
Hudnall; J. Am. Chem. Soc., 2007, 129, 11978-11986. (Year: 2007).*
Lauer; Journal of Organometallic Chemistry 1983, 256, 1-9. (Year: 1983).*
Legare; J. Am. Chem. Soc., 2017, 139, 14714-14723. (Year: 2017).*
Matsuda; J. Am. Chem. Soc. 2013, 135, 4934-4937. (Year: 2013).*
Morris; Adv.Synth. Catal. 2015, 357, 2311-2316. (Year: 2015).*
Wade; Chem. Commun., 2010, 46, 6380-6381. (Year: 2010).*
Bagutski et al., "Mechanistic Studies into Amine-Mediated Electrophilic Arene Borylation and Its Application in MIDA Boronate Synthesis," *J. Am. Chem. Soc.*, 2013, 135:474-487.
Berkefeld et al., "Tandem Frustrated Lewis Pair/Tris(pentafluorophenyl)borane-Catalyzed Deoxygenative Hydrosilylation of Carbon Dioxide," *J. Am. Chem. Soc.*, 2010, 132:10660-10661.
Chan et al., "New N- and O-Arylations with Phenylboronic Acids and Cupric Acetate," *Tetrahedron Letters*, 1998, 39:2933-2936.
Chase et al., "Metal-Free Catalytic Hydrogenation," *Angew. Chem.*, 2007, 119:8196-8199.
Chernichenko et al., "A frustrated-Lewis-pair approach to catalytic reduction of alkynes to cis-alkenes," *Nature Chemistry*, 2013, 5:718-723.
Chernichenko et al., "Hydrogen activation by 2-boryl-N,N-dialkylanilines: a revision of Piers' *ansa*-aminoborane," *Dalton Trans.*, 2012, 41:9029-9032.
Chernichenko et al., "Intramolecular Frustrated Lewis Pair with the Smallest Boryl Site Reversible H2 Addition and Kinetic Analysis," *Angewandte Chemie International Edition*, 2015, 54:1749-1753.
Chernichenko et al., "Intramolecular Frustrated Lewis Pair with the Smallest Boryl Site: Reversible H$_2$ Addition and Kinetic Analysis," *Angew. Chem. Int. Ed.*, 2015, 15:1749-1753.
Cho et al., "Remarkably Selective Iridium Catalysts for the Elaboration of Aromatic C-H Bonds," *Science*, 2002, 295:305-308.

(Continued)

*Primary Examiner* — Daniel R Carcanague

(74) *Attorney, Agent, or Firm* — Norton Rose Fulbright US LLP

(57) ABSTRACT

Precatalysts of formula I and IV, and processes for the functionalization of SP2-carbons using the same are described herein. The precatalysts comprise a fluoroborate salt protected intramolecular frustrated lewis pair (FLP). The precatalysts are bench stable with improved stability towards moisture and/or air. The precatalysts can be used to generate in situ the corresponding FLP catalyst.

21 Claims, 4 Drawing Sheets

(56) References Cited

OTHER PUBLICATIONS

Figure 1:
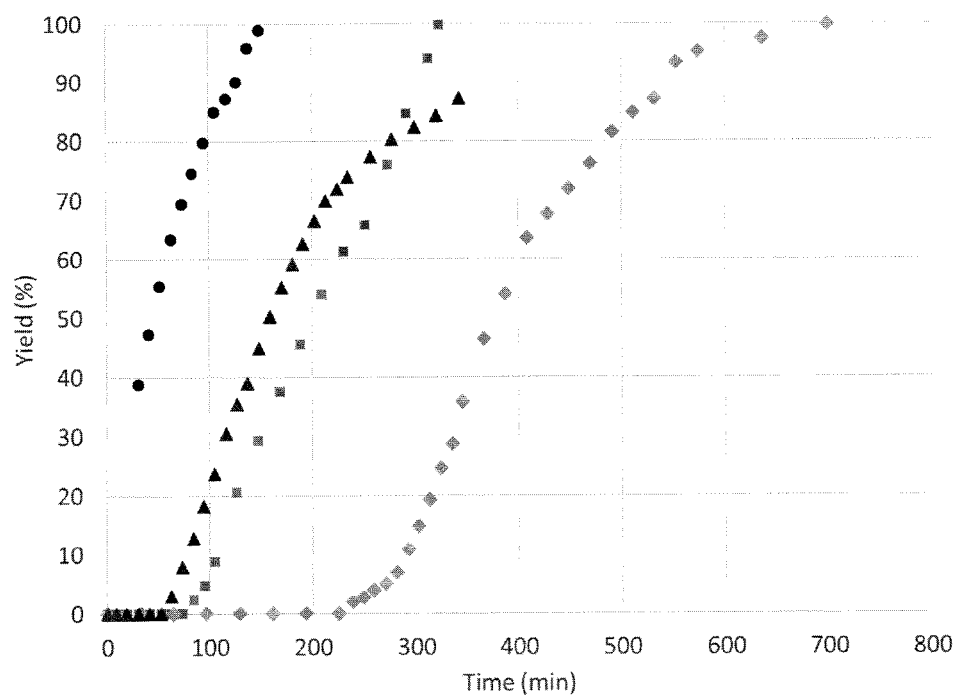

Courtemanche et al., "A Highly Active Phosphine-Borane Organocatalyst for the Reduction of $CO_2$ to Methanol Using Hydroboranes," *J. Am. Chem. Soc.*, 2013, 135:9326-9329.
Courtemanche et al., "A Tris(triphenylphosphine) aluminum Ambiphilic Precatalyst for the Reduction of Carbon Dioxide with Catecholborane," *Organometallics*, 2013, 32:6804-6811.
Courtemanche et al., "Intramolecular B/N frustrated Lewis pairs and the hydrogenation of carbon dioxide," *Chem. Comm.*, 2015, 15:9797-9800.
Courtemanche et al., "Reducing CO2 to Methanol Using Frustrated Lewis Pairs: On the Mechanism of Phosphine-Borane-Mediated Hydroboration of CO2," *J. Am. Chem. Soc.*, 2014, 136:10708-10717.
Das Neves Gomes et al., "Metal-Free Reduction of CO2 with Hydroboranes: Two Efficient Pathways at Play for the Reduction of CO2 to Methanol," *Chem. Eur. J.*, 2014, 20:7098-7106.
Declercq et al., "Hydroboration of carbon Dioxide Using Ambiphilic Phosphine borane Catalysts: On the Role of the Formaldehyde Adduct," *ACS Catal.*, 2015, 5:2513-2520.
Del Grosso et al., "Chelate Restrained Boron cations for Intermolecular Electrophilic Arene Borylation," *Organometallics*, 2010, 29:241-249.
Del Grosso et al., "Pinacol Boronates by Direct Arene Borylation with Borenium Cations," *Angew. Chem. Int. Ed.*, 2011, 50:2102-2106.
Dombray et al., "Iron-Catalyzed C-H Borylation of Arenes," *J. Am. Chem. Soc.*, 2015, 137:4062-4065.
Erker & Stephan, "Frustrated Lewis Pairs I Uncovering and Understanding," Springer:Berlin, Heidelberg, 2013, 332:85-110.
Furukawa et al., "Nickel-Catalyzed borylation of arenes and indoles via C-H bond cleavage," *Chem. Commun.*, 2015, 51:6508-6511.
Greb et al. "Metal-free Catalytic Olefin Hydrogenation: Low-Temperature $H_2$ Activation by Frustrated Lewis Pairs," *Angew. Chem.*, 2012, 124:10311-10315.
Hall, "Structure, Properties, Preparation of Boronic Acid Derivatives Overview of Their Reactions and applications," *Bornic Acids*, $2^{nd}$ Ed.; Wiley-VCH: Weinhein, 2011.
Hatanaka et al., "C-H Bond activation/Borylation of Furans and Thiophenes catalyzed by a Half-Sandwich Iron N-Heterocyclic Carbene complex," *Chem. Asian. J.*, 2010, 5:1657-1666.
Houghton et al., "Direct observation of a borane-silane complex involved in frustrated Lewis-pair-mediated hydrosilylations," *Nature Chemistry*, 2014, 6:983-988.
Hounjet et al., "Combinations of Ethers and $B(C_6F_5)^3$ Function as Hydrogenation Catalysts," *Angew. Chem.*, 2013, 125:7640-7643.
International Conference on Harmonisation of Technical Requirements for Regitration of Pharmaceuticals for Human Use—Q3D Elemental Impurities, Accessed from the Internet on Jun. 20, 2015, <http://fda.gov/downloads/drugs/guidancecomplianceregulatoryinformation/guidances/ucm371025.pdf>.
International Search Report and Written Opinion issued in International Patent Application No. PCT/Ca2016/000318, dated Mar. 31, 2017.
Ishiyama et al., "A Stoichiometric Aromatic C-H Borylation Catalyzed by Iridium (I)/2,2'-Bipyridine Complexes at Room Temperature," *Angew. Chem. Int. Ed.*, 2002, 41(16):3056-3058.
Ishiyama et al., "Mild Iridium-Catalyzed Borylation of Arenes. High Turnover Numbers, Room Temperature Reactions, and Isolation of a Potential Intermediate," *J. Am. Chem. Soc.*, 2002, 124(3):390-391.
Ishiyama et al., "Room temperature borylation of arenes and heteroarenes using stoichiometric amounts of pinacolborane catalyzed by iridium complexes in an inert solvent," *Chem. Commun.*, 2003, 2924-2925.

Lafrance & Fagnou, "Palladium-Catalyzed Benzene Artylation: Incorporation of Catalytic Pivalic Acid as a Proton Shuttle and a Key Element in Catalyst Design," *J. Am. Chem. Soc.*, 2006, 128:16496-16497.
Larsen & Hartwig, "Iridium-Catalyzed C-H Borylation of Heteroarenes: Scope, Regioselectivity, Application to Late-Stage Functionalization, and Mechanism," *J. Am. Chem. Soc.*, 2014, 136:4287-4299.
Legare et al., "Bench Stable Frustrated Lewis Pair Chemistry: Fluoroborate Salts as Precatalysts for the C-H Borylation of Heteroarens," *Chemical Communications*, 2016, 52:5387-5390.
Legare et al., "Cooperative Reactivity of Boron-Containing Molecules and Lewis Bases for Metal Free Catalysis," These, Univeristy Laval, Aug. 2015, URL <http://theses.ulaval.ca/archimede/meta/32015.
Legare et al., "Metal-free catalytic C-H bond activation and borylation of heteroarenes," *Science*, 2015, 349(6247):513-516.
Mandi et al., "Enabling Catalytic Ketone Hydrogenation by Frustrated Lewis Pairs," *J. Am. Chem. Soc.*, 2014, 136:15809-15812.
Mazzacano & Mankad, "Base Metal Catalysts for Photochemical C-H Borylation That Utilize Metal-Metal Cooperativity," *J. Am. Chem. Soc.*, 2013, 135:17258-17261.
Miyaura & Suzuki, "Palladium-Catalyzed Cross-Coupling Reactions of Organoborn Compounds," *Chem. Rev.*, 1995, 95:2457-2483.
Mkhalid et al., "C-H Activation for the Construction of C-B Bonds," *Chem. Rev.*, 2010, 110:890-931.
Obligacion et la., "Cobalt-catalyzed C-H Borylation," *J. Am. Chem. Soc.*, 2014, 136:4133-4136.
Prokofjevs et al., "A Boronium Ion with Exceptional Electrophilicity," *Angew. Chem. Int. Ed.*, 2011, 50:2098-2101.
Rousseaux et al., "Modern Tools for the Synthesis of Complex Bioactive Molecules," John Wiley & Sons, Inc., 2012, pp. 1-32.
Sather et al., "Dosage delivery of sensitive reagents enables glovebox-free synthesis," *Nature*, 2015, 524:208-211.
Spies et al., "Metal-Free Catalytic Hydrogenation of Enamines, Imines, and Conjugated Phosphinoalkenylboranes," *Angew. Chem. Int. Ed.*, 2008, 47:7543-7546.
Stahl et al., "Catalytic Generation of Borenium Ions by Cooperative B-H Bond Activation: The Elusive Direct Electrophilic Borylation of Nitrogen Heterocycles with Pinacolborane," *J. Am. Chem. Soc.*, 2013, 135:10978-10981.
Stephan & Erker, "Frustrated Lewis Pair Chemistry: Development and Perspectives," *Angew. Chem. Int. Ed.*, 2015, 54:6400-6441.
Stephan & Erker, "Frustrated Lewis Pairs: Metal-free Hydrogen Activation and More," *Angew. Chem. Int. Ed.*, 2010, 49:46-76.
Stephan, "Frustrated Lewis Pairs hydrogenation," *Org. Biomol. Chem.*, 2012, 10:5740-5746.
Stephan, "Frustrated Lewis Pairs: From Concept to Catalysis," *Acc. Chem. Res.*, 2015, 48:306-316.
Tajuddin et al., "Iridium-catalyzed C-H borylation of quinolones and unsymmetrical 1,2-disubstituted benzenes: insights into steric and electronic effects on selectivity," *Chem. Sci.*, 2012, 3:3505-3515.
Usluer et al., "Metal Residues in Semiconducting Polymers: Impact on the Performance of Organic Electronic Devices," *ACS Macro Lett.*, 2014, 3:1134-1138.
Vanchura, II et al., "Electronic effects in iridium C-H borylations: insights from unencumbered substrates and variation of boryl ligand and substituents," *Chem. Comm.*, 2010, 46:7724-7726.
Wang & Stephan, "Carbene-9-BBN Ring Expansions as a Route to Intramolecular Frustrated Lewis Pairs for CO2 Reduction," *Chem. Eur. J.*, 2014, 20:3036-3039.
Wang & Stephan, "Phosphine catalyzed reduction of CO2 with boranes," *Chem. Commun.*, 2014, 51:7007-7010.
Welch et al., "Reversible, Metal-Free Hydrogen Activation," *Science*, 2006, 314:1124-1126.
Wencel-Delord & Glorius, "C-H bond activation enables the rapid construction and late-stage diversification of functional molecules," *Nature Chemistry*, 2013, 5:369-375.

* cited by examiner

PRECATALYSTS AND PROCESS FOR THE METAL-FREE FUNCTIONALIZATION OF SP² CARBONS USING THE SAME

CROSS REFERENCE TO RELATED APPLICATIONS

The present application is a national phase under 35 U.S.C. § 371 of International Application No. PCT/CA2016/000318, filed Dec. 15, 2016, which claims the benefit of priority from co-pending U.S. Provisional Application No. 62/267,637, filed on Dec. 15, 2015. The contents of each of the referenced applications are incorporated herein by reference in their entirety.

FIELD

The present disclosure broadly relates to precatalysts and processes for the functionalization of sp²-carbons using the same. More specifically, but not exclusively, the present disclosure relates to precatalysts and metal-free catalytic processes for forming functionalized alkenes, arenes and heteroarenes using the same. The present disclosure also relates to precatalysts for the metal-free borylation of sp² carbons.

BACKGROUND

The selective C—H bond activation and catalytic functionalization of organic molecules is a simple and environmentally benign route for the production of valuable small molecules as well as for the late-stage functionalization of complex chemical architectures.[1-3] Among the different metal-catalyzed C—H functionalization systems, the borylation of organic compounds is a highly important reaction that gives access to valuable chemicals that can be used in opto-electronic systems, in pharmaceuticals or as reagents in processes such as the Suzuki-Miyaura cross-coupling and the Chan-Lam reaction.[4-9]

In recent years, iridium/bipyridine catalytic systems have surpassed other noble metal catalysts as the most reliable and convenient mediators[5, 6, 10-13] for selective C—H bond activation, although these catalysts generate undesirable costs and potential risks to humans.[14] Base-metal alternatives, such as iron, iron/copper, cobalt and nickel catalysts have been reported, but suffer from inferior efficiency as compared to precious metal systems.[15-19]

Electrophilic borylation strategies have also recently emerged but in the current state of things, the generation of boron cations necessitates the use of stoichiometric reagents[20-22] or transition metal-based catalysts[23] or strongly acidic[24] catalysts.

A concept that has attracted considerable attention of late is that of frustrated Lewis pairs (FLPs) as metal-free catalytic systems.[25-28] Indeed, this strategy has been shown to achieve a wide range of reactivity previously exclusive to transition metals in the fields of hydrogenation,[29-37] hydroboration[38-44] and hydrosilylation[45, 46].

More recently, the scope of the FLP reactions has been expanded out of the traditional field of reduction processes and the use of ambiphilic 1-TMP-2-borylbenzene (TMP=2,2,6,6-tetramethylpiperidine)[47] as a metal-free catalyst for the cleavage and borylation of heteroaromatic C—H bonds was reported.[48] Mechanistic investigations have suggested that this catalyst relied on the interaction of the aromatic substrate with the boron atom of 1-TMP-2-borylbenzene, with simultaneous deprotonation by the basic TMP moiety. This mechanism was likened to the "concerted metalation-deprotonation" (CMD) that had been previously proposed by Fagnou and coworkers as the dominant process in the palladium carboxylate-mediated direct arylation reaction.[49] Interestingly, the selectivity of the reaction was found to be dominated by the nucleophilicity of the aromatic substrate and to be complementary to that of most iridium-based systems where the activation is guided by the acidity of the proton to be cleaved.[12, 50]

While metal-free catalysts for C—H activation are an exciting idea, because of their low cost and low toxicity, the applicability of 1-TMP-2-borylbenzene for borylation reactions remains rather limited in view of the moisture sensitivity of the $BH_2$ moiety. The moisture sensitivity, a constant in most FLP chemistry, implies a necessity for handling and storing the catalyst under an inert atmosphere and represents an important obstacle to its implementation.[51]

The present disclosure refers to a number of documents, the contents of which are herein incorporated by reference in their entirety.

SUMMARY

A solution to the aforementioned problems associated with the use of FLPs as metal-free catalytic systems for C—H activation, and more particularly problems associated with the use of 1-TMP-2-borylbenzene for borylation reactions, has been discovered. Broadly, the solution resides in the discovery of precatalyst fluoroborate salts that can be used to generate the corresponding FLP catalyst in situ. Notably, once introduced into a given reaction medium, the B—F bonds of the precatalyst fluoroborate salts can be deprotected to regenerate the catalytically relevant $BH_2$ moieties. A benefit of the precatalyst fluoroborate salts of the present disclosure is that they are more stable to moisture and/or air. In an aspect, the increased stability of the precatalyst fluoroborate salts presents a more efficient platform for the functionalization of sp²-carbons. In an aspect, the efficiency can be in the form of improved ease in handling, storing and/or use of the precatalyst fluoroborate salts for the functionalization of sp²-carbons.

In an aspect, the present disclosure broadly relates to precatalysts and processes for the functionalization of sp²-carbons using the same. More specifically, but not exclusively, the present disclosure relates to precatalysts and metal-free catalytic processes for forming functionalized alkenes, arenes and heteroarenes using the same. The present disclosure also relates to precatalysts for the metal-free borylation of sp² carbons.

The present disclosure, in an aspect, relates to catalytic processes for the metal-free borylation of sp²-carbons. In a further aspect, the present disclosure broadly relates to metal-free catalytic processes for forming borylated alkenes, arenes and heteroarenes. In yet a further aspect, the present disclosure broadly relates to precatalysts for the metal-free borylation of sp² carbons. In yet a further aspect, the present disclosure broadly relates to precatalysts comprising a fluoroborate salt for the metal-free borylation of sp² carbons.

The present disclosure, in an aspect, relates to catalytic processes for effecting $C_{sp2}$—H bond cleavage. In an embodiment, the $C_{sp2}$—H bond cleavage is effected using catalysts comprising a Frustrated Lewis Pair (FLP) that are generated in situ from the corresponding precatalyst fluoroborate salts. In a further embodiment, the precatalysts are used in metal-free processes effecting $C_{sp2}$—H bond cleavage.

The present disclosure, in an aspect, relates to the catalytic dehydrogenative borylation of alkenes, arenes and heteroarenes. In an embodiment of the present disclosure, precatalyst fluoroborate salts are deprotected to generate catalysts including intramolecular FLPs for the dehydrogenative borylation of $sp^2$ carbons. In a further embodiment of the present disclosure, precatalyst fluoroborate salts are deprotected to generate catalysts including intramolecular FLPs for the dehydrogenative borylation of alkenes, arenes and heteroarenes.

The present disclosure, in an aspect includes contacting a precatalytic reagent comprising at least one protected intramolecular Frustrated Lewis Pair, a functionalization reagent, and a substrate comprising a $C_{sp2}$—H bond, under conditions to provide a substrate comprising a functionalized $sp^2$ carbon. In an embodiment of the present disclosure, the protected intramolecular Frustrated Lewis Pair comprises a fluoroborate salt.

The present disclosure, in an aspect includes contacting a precatalytic reagent comprising at least one protected intramolecular Frustrated Lewis Pair, an organoborane reagent, and a substrate comprising a $C_{sp2}$—H bond, under conditions to provide a substrate comprising a borylated $sp^2$ carbon. In an embodiment of the present disclosure, the protected intramolecular Frustrated Lewis Pair comprises a fluoroborate salt.

The present disclosure, in an aspect, relates to the use of organotrifluoroborate salts to protect the organoboron moiety of FLP catalysts. The present disclosure, in a further aspect, relates to the use of organotrifluoroborate salts to protect the organoboron moiety of intramolecular FLP catalysts. In a further aspect, the present disclosure relates to the preparation of fluoroborate derivatives of 1-TMP-2-borylbenzene. In yet a further aspect, the present disclosure relates to fluoroborate derivatives of intramolecular FLP catalysts as stable precursors to active borylation catalysts. In yet a further aspect, the present disclosure relates to the deprotection of the B—F bonds of the fluoroborate derivatives in the reaction medium to regenerate the catalytically relevant $BH_2$ moieties. In yet a further aspect, the present disclosure relates to the in-situ deprotection of the B—F bonds of the fluoroborate derivatives in the reaction medium to regenerate the catalytically relevant $BH_2$ moieties.

In an embodiment, the present disclosure includes a precatalyst for the functionalization of a $sp^2$-carbon, the precatalyst having the formula:

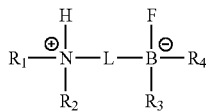

wherein:
R$_1$ and R$_2$ are independently, C$_{1-15}$alkyl, C$_{3-15}$branched alkyl, C$_{6-18}$aryl, C$_{6-15}$aryl having at least one C$_{1-10}$alkyl substituent, C$_{5-8}$cycloalkyl; C$_{5-8}$cycloalkyl having at least one C$_{1-10}$alkyl substituent; or
R$_1$ and R$_2$ are linked together to form a nitrogen containing ring system, wherein the nitrogen containing ring system is optionally substituted by one or more C$_{1-10}$alkyl groups; or
R$_1$ and R$_2$ are linked together to form a morpholine, piperazine, N'-alkyl piperazine, or thiomorpholine ring system that is optionally substituted by one or more C$_{1-10}$alkyl groups;

R$_3$ and R$_4$ are independently hydrogen, halogen, C$_{1-15}$alkyl, C$_{3-15}$branched alkyl, C$_{6-18}$aryl, C$_{6-18}$aryl having at least one C$_{1-10}$alkyl substituent, C$_{5-8}$cycloalkyl; C$_{5-8}$cycloalkyl having at least one C$_{1-10}$alkyl substituent, OR$_5$, SR$_6$; or
R$_3$ and R$_4$ are linked together to form a boron containing ring system, wherein the boron containing ring system is optionally substituted by one or more C$_{1-10}$alkyl groups;
R$_5$ and R$_6$ are independently hydrogen, C$_{1-15}$alkyl or C$_{3-15}$branched alkyl; R$_7$ and R$_8$ are independently hydrogen or C$_{1-15}$alkyl; and
L is a heteroarene, arene, or a carbon chain (C$_1$ trough C$_{20}$) which can be linear, cyclic or branched and may comprise heteroatoms, wherein the heteroarene, arene or carbon chain may optionally be substituted with one or more substituents selected from halogen, C$_{1-15}$alkyl, C$_{3-15}$branched alkyl, aryl, OCF$_3$, CF$_3$, OR$_7$ and SR$_8$; with the proviso that $^+$NH and $^-$BF are in a vicinal position relative to each other;
L is a polymer comprising monomeric repeating units having an aryl group, with the proviso that $^+$NH and $^-$BF are in a vicinal position relative to each other on the aryl groups; or
L is a solid support, with the proviso that $^+$NH and $^-$BF are in a vicinal position relative to each other.

In an embodiment, the present disclosure includes a precatalyst for the functionalization of a $sp^2$-carbon, the precatalyst having the formula:

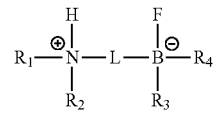

wherein:
R$_1$ and R$_2$ are independently, C$_{1-15}$alkyl, C$_{3-15}$branched alkyl, C$_{6-18}$aryl, C$_{6-18}$aryl having at least one C$_{1-10}$alkyl substituent, C$_{5-8}$cycloalkyl; C$_{5-8}$cycloalkyl having at least one C$_{1-10}$alkyl substituent; or
R$_1$ and R$_2$ are linked together to form a nitrogen containing ring system, wherein the nitrogen containing ring system is optionally substituted by one or more C$_{1-10}$alkyl groups; or
R$_1$ and R$_2$ are linked together to form a morpholine, piperazine, N'-alkyl piperazine, or thiomorpholine ring system that is optionally substituted by one or more C$_{1-10}$alkyl groups;
R$_3$ and R$_4$ are independently hydrogen, halogen, C$_{1-15}$alkyl, C$_{3-15}$branched alkyl, C$_{6-18}$aryl, C$_{6-18}$aryl having at least one C$_{1-10}$alkyl substituent, C$_{5-8}$cycloalkyl; C$_{5-8}$cycloalkyl having at least one C$_{1-10}$alkyl substituent, OR$_5$, SR$_6$; or
R$_3$ and R$_4$ are linked together to form a boron containing ring system, wherein the boron containing ring system is optionally substituted by one or more C$_{1-10}$alkyl groups;
R$_5$ and R$_6$ are independently hydrogen, C$_{1-15}$alkyl or C$_{3-15}$branched alkyl;
R$_7$ and R$_8$ are independently hydrogen or C$_{1-15}$alkyl; and
L is a heteroarene or arene, wherein the heteroarene or arene may optionally be substituted with one or more substituents selected from halogen, C$_{1-15}$alkyl, C$_{3-5}$branched alkyl, aryl, OCF$_3$, CF$_3$, OR$_7$ and SR$_8$;

with the proviso that $^+$NH and $^-$BF are in a vicinal position relative to each other;

L is a polymer comprising monomeric repeating units having an aryl group, with the proviso that $^+$NH and $^-$BF are in a vicinal position relative to each other on the aryl groups; or L is a solid support, with the proviso that $^+$NH and $^-$BF are in a vicinal position relative to each other.

In an embodiment, the present disclosure includes a precatalyst for the functionalization of a sp$^2$-carbon, the precatalyst having a structure defined by Formula I:

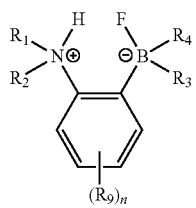

Formula I wherein:
- $R_1$ and $R_2$ are independently, $C_{1-15}$alkyl, $C_{3-15}$branched alkyl, $C_{6-18}$aryl, $C_{6-18}$aryl having at least one $C_{1-10}$alkyl substituent, $C_{5-8}$cycloalkyl; $C_{5-8}$cycloalkyl having at least one $C_{1-10}$alkyl substituent; or
- $R_1$ and $R_2$ are linked together to form a nitrogen containing ring system, wherein the nitrogen containing ring system is optionally substituted by one or more $C_{1-10}$alkyl groups; or
- $R_1$ and $R_2$ are linked together to form a morpholine, piperazine, N'-alkyl piperazine, or thiomorpholine ring system that is optionally substituted by one or more $C_{1-10}$alkyl groups;
- $R_3$ and $R_4$ are independently hydrogen, halogen, $C_{1-15}$alkyl, $C_{3-15}$branched alkyl, $C_{6-18}$aryl, $C_{6-18}$aryl having at least one $C_{1-10}$alkyl substituent, $C_{5-8}$cycloalkyl; $C_{5-8}$cycloalkyl having at least one $C_{1-10}$alkyl substituent, $OR_5$, $SR_6$; or
- $R_3$ and $R_4$ are linked together to form a boron containing ring system, wherein the boron containing ring system is optionally substituted by one or more $C_{1-10}$alkyl groups;
- $R_5$ and $R_6$ are independently hydrogen, $C_{1-15}$alkyl or $C_{3-15}$branched alkyl;
- $R_9$ is hydrogen, halogen, $C_{1-15}$alkyl, $C_{3-15}$branched alkyl, aryl, $OCF_3$, $CF_3$, $OR_5$ or $SR_6$; wherein when $R_9$ is present more than once, each $R_9$ is independently hydrogen, halogen, $C_{1-15}$alkyl, $C_{3-15}$branched alkyl, aryl, $OCF_3$, $CF_3$, $OR_5$ or $SR_6$; and
- n is an integer ranging from 1 to 5.

In an embodiment, the present disclosure includes a precatalyst for the functionalization of a sp$^2$-carbon, the precatalyst having a structure defined by Formula I:

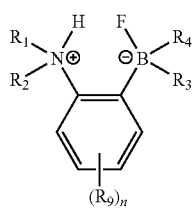

Formula I wherein:
- $R_1$ and $R_2$ are independently, $C_{1-15}$alkyl, $C_{3-15}$branched alkyl, $C_{6-18}$aryl, $C_{6-18}$aryl having at least one $C_{1-10}$alkyl substituent, $C_{5-8}$cycloalkyl; $C_{5-8}$cycloalkyl having at least one $C_{1-10}$alkyl substituent; or
- $R_1$ and $R_2$ are linked together to form a nitrogen containing ring system, wherein the nitrogen containing ring system is optionally substituted by one or more $C_{1-10}$alkyl groups;
- $R_3$ and $R_4$ are independently hydrogen, halogen, $C_{1-15}$alkyl, $C_{3-15}$branched alkyl, $C_{6-18}$aryl, $C_{6-18}$aryl having at least one $C_{1-10}$alkyl substituent, $C_{5-8}$cycloalkyl; $C_{5-8}$cycloalkyl having at least one $C_{1-10}$alkyl substituent, $OR_5$, $SR_6$; or
- $R_3$ and $R_4$ are linked together to form a boron containing ring system, wherein the boron containing ring system is optionally substituted by one or more $C_{1-10}$alkyl groups;
- $R_5$ and $R_6$ are independently hydrogen, $C_{1-15}$alkyl or $C_{3-15}$branched alkyl;
- $R_9$ is hydrogen, halogen, $C_{1-15}$alkyl, $C_{3-15}$branched alkyl, aryl, $OCF_3$, $CF_3$, $OR_5$ or $SR_6$; wherein when $R_9$ is present more than once, each $R_9$ is independently hydrogen, halogen, $C_{1-15}$alkyl, $C_{3-15}$branched alkyl, aryl, $OCF_3$, $CF_3$, $OR_5$ or $SR_6$; and n is an integer ranging from 1 to 5.

In an embodiment, the present disclosure includes a precatalyst for the functionalization of a sp$^2$-carbon, the precatalyst having a structure defined by Formula II:

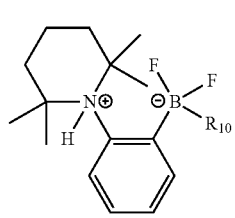

Formula II wherein:
- $R_{10}$ is F or $OR_{11}$; and
- $R_{11}$ is H, $C_{1-15}$alkyl or $C_{3-15}$branched alkyl.

In an embodiment, the present disclosure includes a precatalyst for the functionalization of a sp$^2$-carbon, the precatalyst having the structure:

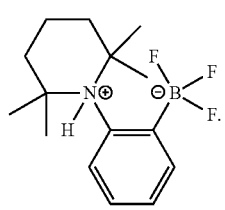 [SMILES: CC1(C)CCCC(C)(C)[NH+]1c1ccccc1[B-](F)(F)F]

In an embodiment, the present disclosure includes a precatalyst for the functionalization of a sp$^2$-carbon, the precatalyst having the structure:

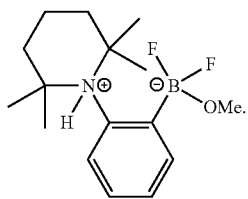 [SMILES: CO[B-](F)(F)c1ccccc1[NH+]1C(C)(C)CCCC1(C)C]

In an embodiment, the present disclosure includes a precatalyst for the functionalization of a sp²-carbon, the precatalyst having the structure:

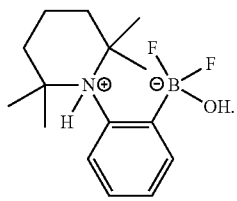 [SMILES: CC1(C)CCCC(C)(C)[NH+]1c1ccccc1[B-](O)(F)F]

In an embodiment, the present disclosure includes a precatalyst for the functionalization of a sp²-carbon, the precatalyst having the structure defined by Formula III:

Formula III wherein
- $R_{12}$ is H, halogen, $C_{1-15}$alkyl, $C_{3-15}$branched alkyl, aryl, $OCF_3$, $CF_3$, $OR_5$ or $SR_6$; and
- $R_5$ and $R_6$ are independently hydrogen, $C_{1-15}$alkyl or $C_{3-15}$branched alkyl.

In an embodiment, the present disclosure includes a precatalyst for the functionalization of a sp²-carbon, the precatalyst having the structure:

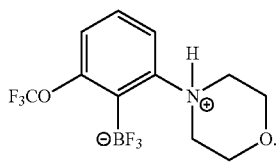

In an embodiment, the present disclosure includes a precatalyst for the functionalization of a sp²-carbon, the precatalyst having the structure:

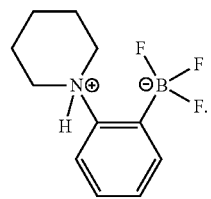 [SMILES: F[B-](F)(F)c1ccccc1[NH+]1CCCCC1]

In an embodiment, the present disclosure includes a precatalyst for the functionalization of a sp²-carbon, the precatalyst having the structure:

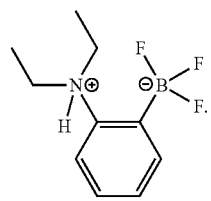

In an embodiment, the present disclosure includes a precatalyst for the functionalization of a sp²-carbon, the precatalyst having the structure:

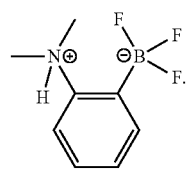

In an embodiment, the present disclosure includes a precatalyst for the functionalization of a sp²-carbon, the precatalyst having the structure defined by Formula IV:

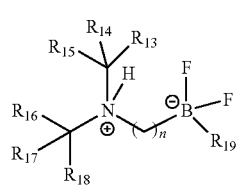

Formula IV wherein:
- $R_{13}$, $R_{14}$, $R_{16}$ and $R_{17}$ are independently $C_{1-5}$alkyl;
- $R_{15}$ and $R_{18}$ are independently H or $C_{1-5}$alkyl; or
- $R_{15}$ and $R_{18}$ are linked together to form a nitrogen containing ring system, wherein the nitrogen containing ring system is optionally further substituted by one or more $C_{1-10}$alkyl groups; or
- $R_{15}$ and $R_{18}$ are linked together to form a morpholine, piperazine, N'-alkyl piperazine, or thiomorpholine ring system that is optionally substituted by one or more $C_{1-10}$alkyl groups;
- $R_{19}$ is F or $OR_{20}$;
- $R_{20}$ is H, $C_{1-15}$alkyl or $C_{3-15}$branched alkyl; and
- n is 1 or 2.

In an embodiment, the present disclosure includes a precatalyst for the functionalization of a sp²-carbon, the precatalyst having the structure defined by Formula V:

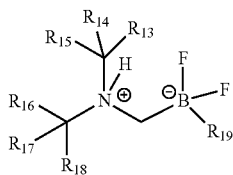

Formula V wherein:
$R_{13}$, $R_{14}$, $R_{16}$ and $R_{17}$ are independently $C_{1-5}$alkyl;
$R_{15}$ and $R_{18}$ are independently H or $C_{1-5}$alkyl; or
$R_{15}$ and $R_{18}$ are linked together to form a nitrogen containing ring system, wherein the nitrogen containing ring system is optionally further substituted by one or more $C_{1-10}$alkyl groups; or
$R_{15}$ and $R_{18}$ are linked together to form a morpholine, piperazine, N'-alkyl piperazine, or thiomorpholine ring system that is optionally substituted by one or more $C_{1-10}$alkyl groups;
$R_{19}$ is F or $OR_{20}$; and
$R_{20}$ is H, $C_{1-15}$alkyl or $C_{3-15}$branched alkyl.

In an embodiment, the present disclosure includes a precatalyst for the functionalization of a $sp^2$-carbon, the precatalyst having the structure defined by Formula VI:

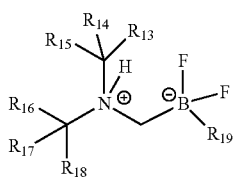

Formula VI wherein:
$R_{13}$, $R_{14}$, $R_{16}$ and $R_{17}$ are independently $C_{1-5}$alkyl;
$R_{15}$ and $R_{18}$ are independently H or $C_{1-5}$alkyl; or
$R_{15}$ and $R_{18}$ are linked together to form a nitrogen containing ring system, wherein the nitrogen containing ring system is optionally further substituted by one or more $C_{1-10}$alkyl groups;
$R_{19}$ is F or $OR_{20}$; and
$R_{20}$ is H, $C_{1-5}$alkyl or $C_{3-15}$branched alkyl.

In an embodiment, the present disclosure includes a catalytic process for the functionalization of a $sp^2$ carbon, the process comprising contacting a precatalyst of the present disclosure, a functionalization reagent, and a substrate comprising a $sp^2$—H carbon, under conditions to provide a substrate comprising a functionalized $sp^2$ carbon. In a further embodiment of the present disclosure, the substrate is an alkene, an arene or a heteroarene. In yet a further embodiment of the present disclosure, the functionalization reagent is an organoborane reagent. In yet a further embodiment of the present disclosure, the organoborane reagent is HBPin, HBCat or 9BBN. In yet further embodiments of the present disclosure, the precatalyst is present from about 1 mol % to about 20 mol % or at any mol % or any range derivable therein. In more particular embodiments of the present disclosure, the precatalyst is present at about 1.0 mol %, about 1.1 mol %, about 1.2 mol %, about 1.3 mol %, about 1.4 mol %, about 1.5 mol %, about 1.6 mol %, about 1.7 mol %, about 1.8 mol %, about 1.9 mol %, about 2.0 mol %, about 2.1 mol %, about 2.2 mol %, about 2.3 mol %, about 2.4 mol %, about 2.5 mol %, about 2.6 mol %, about 2.7 mol %, about 2.8 mol %, about 2.9 mol %, about 3.0 mol %, about 3.1 mol %, about 3.2 mol %, about 3.3 mol %, about 3.4 mol %, about 3.5 mol %, about 3.6 mol %, about 3.7 mol %, about 3.8 mol %, about 3.9 mol %, about 4.0 mol %, about 4.1 mol %, about 4.2 mol %, about 4.3 mol %, about 4.4 mol %, about 4.5 mol %, about 4.6 mol %, about 4.7 mol %, about 4.8 mol %, about 4.9 mol %, about 5.0 mol %, about 5.1 mol %, about 5.2 mol %, about 5.3 mol %, about 5.4 mol %, about 5.5 mol %, about 5.6 mol %, about 5.7 mol %, about 5.8 mol %, about 5.9 mol %, about 6.0 mol %, about 6.1 mol %, about 6.2 mol %, about 6.3 mol %, about 6.4 mol %, about 6.5 mol %, about 6.6 mol %, about 6.7 mol %, about 6.8 mol %, about 6.9 mol %, about 7.0 mol %, about 7.1 mol %, about 7.2 mol %, about 7.3 mol %, about 7.4 mol %, about 7.5 mol %, about 7.6 mol %, about 7.7 mol %, about 7.8 mol %, about 7.9 mol %, about 8.0 mol %, about 8.1 mol %, about 8.2 mol %, about 8.3 mol %, about 8.4 mol %, about 8.5 mol %, about 8.6 mol %, about 8.7 mol %, about 8.8 mol %, about 8.9 mol %, about 9.0 mol %, about 9.1 mol %, about 9.2 mol %, about 9.3 mol %, about 9.4 mol %, about 9.5 mol %, about 9.6 mol %, about 9.7 mol %, about 9.8 mol %, about 9.9 mol %, about 10.0 mol %, about 10.1 mol %, about 10.2 mol %, about 10.3 mol %, about 10.4 mol %, about 10.5 mol %, about 10.6 mol %, about 10.7 mol %, about 10.8 mol %, about 10.9 mol %, about 11.0 mol %, about 11.1 mol %, about 11.2 mol %, about 11.3 mol %, about 11.4 mol %, about 11.5 mol %, about 11.6 mol %, about 11.7 mol %, about 11.8 mol %, about 11.9 mol %, about 12.0 mol %, about 12.1 mol %, about 12.2 mol %, about 12.3 mol %, about 12.4 mol %, about 12.5 mol %, about 12.6 mol %, about 12.7 mol %, about 12.8 mol %, about 12.9 mol %, about 13.0 mol %, about 13.1 mol %, about 13.2 mol %, about 13.3 mol %, about 13.4 mol %, about 13.5 mol %, about 13.6 mol %, about 13.7 mol %, about 13.8 mol %, about 13.9 mol %, about 14.0 mol %, about 14.1 mol %, about 14.2 mol %, about 14.3 mol %, about 14.4 mol %, about 14.5 mol %, about 14.6 mol %, about 14.7 mol %, about 14.8 mol %, about 14.9 mol %, about 15.0 mol %, about 15.1 mol %, about 15.2 mol %, about 15.3 mol %, about 15.4 mol %, about 15.5 mol %, about 15.6 mol %, about 15.7 mol %, about 15.8 mol %, about 15.9 mol %, about 16.0 mol %, about 16.1 mol %, about 16.2 mol %, about 16.3 mol %, about 16.4 mol %, about 16.5 mol %, about 16.6 mol %, about 16.7 mol %, about 16.8 mol %, about 16.9 mol %, about 17.0 mol %, about 17.1 mol %, about 17.2 mol %, about 17.3 mol %, about 17.4 mol %, about 17.5 mol %, about 17.6 mol %, about 17.7 mol %, about 17.8 mol %, about 17.9 mol %, about 18.0 mol %, about 18.1 mol %, about 18.2 mol %, about 18.3 mol %, about 18.4 mol %, about 18.5 mol %, about 18.6 mol %, about 18.7 mol %, about 18.8 mol %, about 18.9 mol %, about 19.0 mol %, about 19.1 mol %, about 19.2 mol %, about 19.3 mol %, about 19.4 mol %, about 19.5 mol %, about 19.6 mol %, about 19.7 mol %, about 19.8 mol %, about 19.9 mol %, about 20.0 mol %, In an embodiment, the present disclosure includes a catalytic process for the dehydrogenative functionalization of a $sp^2$ carbon, the process comprising contacting a precatalyst of the present disclosure, a functionalization reagent, and a substrate comprising a $sp^2$—H carbon, under conditions to provide a substrate comprising a functionalized $sp^2$ carbon. In a further embodiment of the present disclosure, the substrate is an alkene, an arene or a heteroarene. In yet a further embodiment of the present disclosure, the functionalization reagent is an organoborane reagent. In yet a further embodiment of the present disclosure, the organoborane reagent is HBPin, HBCat or 9BBN. In yet further embodiments of the present disclosure, the precatalyst is present from about 1 mol % to about 20 mol % or at any mol % or any range derivable therein. In more particular embodiments of the present disclosure, the precatalyst is present at about 1.0 mol %, about 1.1 mol %, about 1.2 mol %, about 1.3 mol %, about 1.4 mol %, about 1.5 mol %, about 1.6 mol %, about 1.7 mol %, about 1.8 mol %, about 1.9 mol %, about 2.0 mol %, about 2.1 mol %, about 2.2 mol %, about 2.3 mol %, about 2.4 mol %, about 2.5 mol %, about 2.6 mol %, about 2.7 mol %, about 2.8 mol %, about 2.9 mol %, about 3.0 mol %, about 3.1 mol %, about 3.2 mol %, about 3.3 mol %, about 3.4 mol %, about 3.5 mol %, about 3.6 mol %, about 3.7 mol %, about 3.8 mol %, about 3.9 mol %, about 4.0 mol %, about 4.1 mol %, about 4.2 mol %, about 4.3 mol %, about 4.4 mol %, about 4.5 mol %, about 4.6 mol %, about 4.7 mol %, about 4.8 mol %, about 4.9 mol %, about 5.0 mol %, about 5.1 mol %, about 5.2 mol %, about 5.3 mol %, about 5.4 mol %, about 5.5 mol %, about 5.6 mol %, about 5.7 mol %, about 5.8 mol %, about 5.9 mol %, about 6.0 mol %, about 6.1 mol %, about 6.2 mol %, about 6.3 mol %, about 6.4 mol %, about 6.5 mol %, about 6.6 mol %, about 6.7 mol %, about 6.8 mol %, about 6.9 mol %, about 7.0 mol %, about 7.1 mol %, about 7.2 mol %, about 7.3 mol %, about 7.4 mol %, about 7.5 mol %, about 7.6 mol %, about 7.7 mol %, about 7.8 mol %, about 7.9 mol %, about 8.0 mol %, about 8.1 mol %, about 8.2 mol %, about 8.3 mol %, about 8.4 mol %, about 8.5 mol %, about 8.6 mol %, about 8.7 mol %, about 8.8 mol %, about 8.9 mol %, about 9.0 mol %, about 9.1 mol %, about 9.2 mol %, about 9.3 mol %, about 9.4 mol %, about 9.5 mol %, about 9.6 mol %, about 9.7 mol %, about 9.8 mol %, about 9.9 mol %, about 10.0 mol %, about 10.1 mol %, about 10.2 mol %, about 10.3 mol %, about 10.4 mol %, about 10.5 mol %, about 10.6 mol %, about 10.7 mol %, about 10.8 mol %, about 10.9 mol %, about 11.0 mol %, about 11.1 mol %, about 11.2 mol %, about 11.3 mol %, about 11.4 mol %, about 11.5 mol %, about 11.6 mol %, about 11.7 mol %, about 11.8 mol %, about 11.9 mol %, about 12.0 mol %, about 12.1 mol %, about 12.2 mol %, about 12.3 mol %, about 12.4 mol %, about 12.5 mol %, about 12.6 mol %, about 12.7 mol %, about 12.8 mol %, about 12.9 mol %, about 13.0 mol %, about 13.1 mol %, about 13.2 mol %, about 13.3 mol %, about 13.4 mol %, about 13.5 mol %, about 13.6 mol %, about 13.7 mol %, about 13.8 mol %, about 13.9 mol %, about 14.0 mol %, about 14.1 mol %, about 14.2 mol %, about 14.3 mol %, about 14.4 mol %, about 14.5 mol %, about 14.6 mol %, about 14.7 mol %, about 14.8 mol %, about 14.9 mol %, about 15.0 mol %, about 15.1 mol %, about 15.2 mol %, about 15.3 mol %, about 15.4 mol %, about 15.5 mol %, about 15.6 mol %, about 15.7 mol %, about 15.8 mol %, about 15.9 mol %, about 16.0 mol %, about 16.1 mol %, about 16.2 mol %, about 16.3 mol %, about 16.4 mol %, about 16.5 mol %, about 16.6 mol %, about 16.7 mol %, about 16.8 mol %, about 16.9 mol %, about 17.0 mol %, about 17.1 mol %, about 17.2 mol %, about 17.3 mol %, about 17.4 mol %, about 17.5 mol %, about 17.6 mol %, about 17.7 mol %, about 17.8 mol %, about 17.9 mol %, about 18.0 mol %, about 18.1 mol %, about 18.2 mol %, about 18.3 mol %, about 18.4 mol %, about 18.5 mol %, about 18.6 mol %, about 18.7 mol %, about 18.8 mol %, about 18.9 mol %, about 19.0 mol %, about 19.1 mol %, about 19.2 mol %, about 19.3 mol %, about 19.4 mol %, about 19.5 mol %, about 19.6 mol %, about 19.7 mol %, about 19.8 mol %, about 19.9 mol %, about 20.0 mol %.

The foregoing and other advantages and features of the present disclosure will become more apparent upon reading of the following non-restrictive description of illustrative embodiments thereof, given by way of example only with reference to the accompanying drawings/figures.

BRIEF DESCRIPTION OF THE DRAWINGS/FIGURES

In the appended drawings/figures:

FIG. 1 is an illustration of the $^1$H NMR monitoring of the borylation reaction of 1-methylpyrrole catalyzed by ambiphilic fluoroborate salts 3a-c using HBPin. The precatalyst (0.01 mmol) was mixed with HBPin (0.195 mmol), 1-methylpyrrole (0.195 mmol) and hexamethylbenzene (internal standard) in 0.4 mL $CDCl_3$. The reaction mixture was introduced into a J-Young NMR tube and followed by $^1$H NMR (400 MHz) at 80° C. Legend: 1-TMP-2-borylbenzene (●), 3a (♦), 3b (■), 3c (▲).

Figure 2:
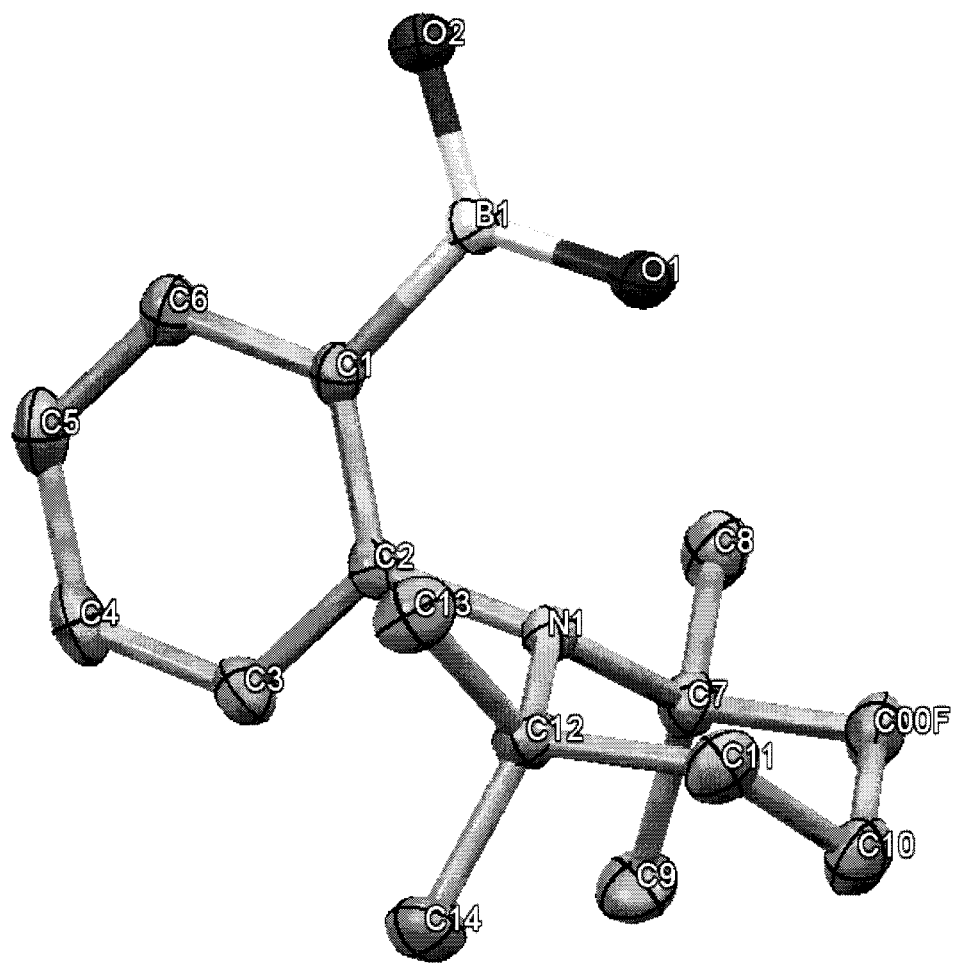

FIG. 2 is an illustration of an ORTEP structure of (2-TMP-benzene) boronic acid (2) with anisotropic atomic displacement ellipsoids at 50% probability level. Hydrogen atoms were omitted for clarity. Selected bond lengths [Å] and angles [°]: O1-B1=1.3682(10); O2-B1=1.3535(10); C1-B1=1.5794(11); N1-C2=1.4595(10); O2-B1-O1=121.55(7); O2-B1-C1=118.24(7); O1-B1-C1=120.21(7); C2-C1-B1=123.41(7); C6-C1-B1=118.22(7); C3-C2-N1=122.17(7); C1-C2-N1=118.36(6).

Figure 3:
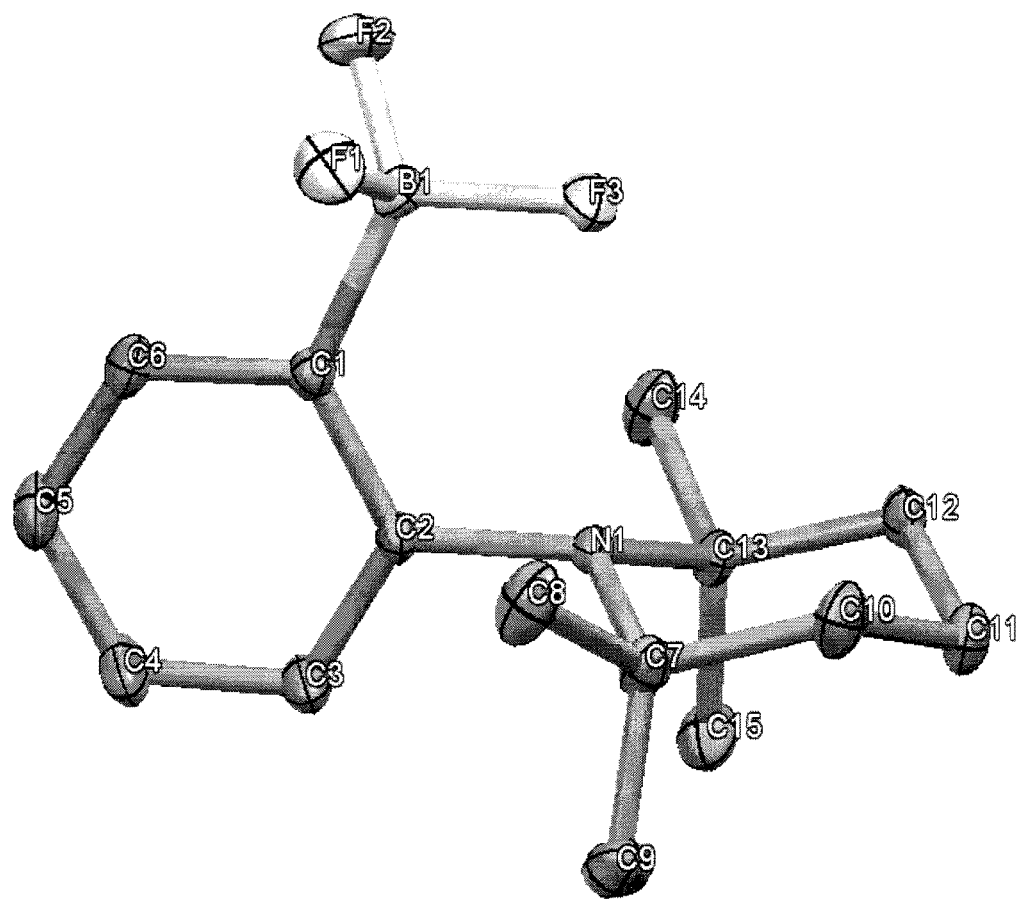

FIG. 3 is an illustration of an ORTEP structure of 1-(Trifluoroborato)-2-TMP-benzene (3a) with anisotropic atomic displacement ellipsoids at 50% probability level. Hydrogen atoms were omitted for clarity. Selected bond lengths [Å] and angles [° ]:F3-B1=1.4383(12); F1-B1=1.4066(13); F2-B1=1.3949(13); N1-C2=1.4883(11); C1-B1=1.6298(15); F2-B1-F1=108.74(8); F2-B1-F3=107.65(8); F1-B1-F3=107.46(9); F2-B1-C1=110.70(9); F1-B1-C1=109.79(8); F3-B1-C1=112.37(8); C2-C1-B1=128.39(8); C6-C1-B1=115.91(8); C3-C2-N1=120.03(8); C1-C2-N1=117.30(8).

Figure 4:
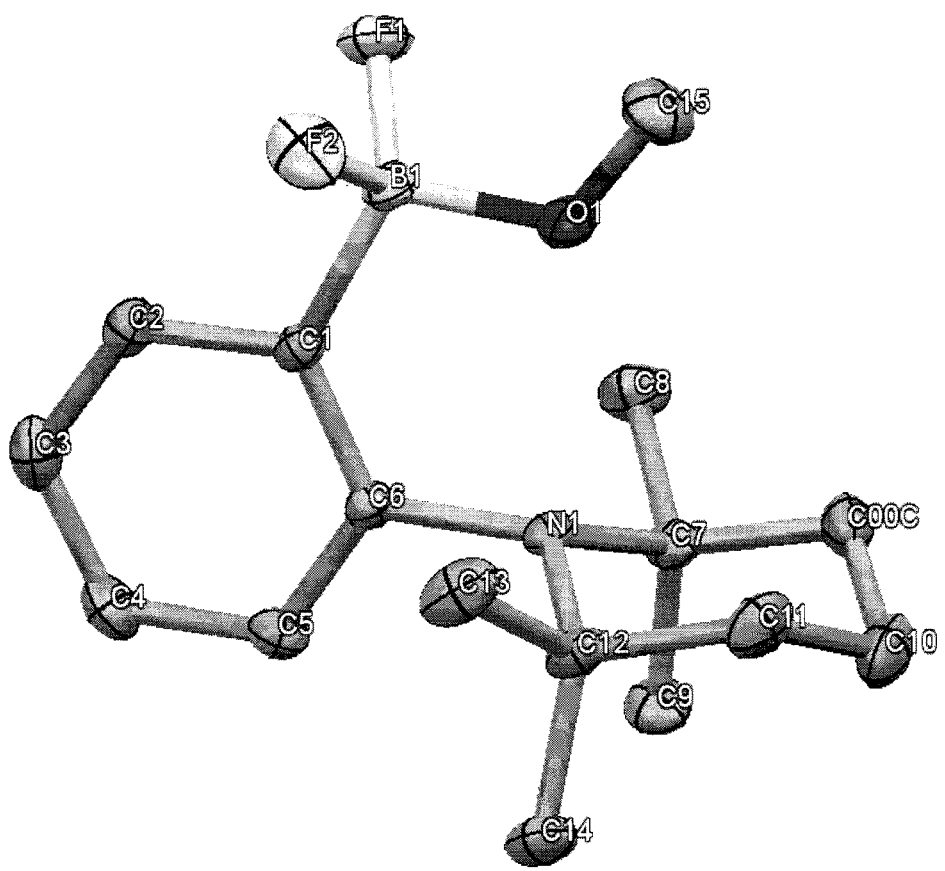

FIG. 4 is an illustration of an ORTEP structure of 1-(Difluoromethoxyborato)-2-TMP-benzene (3b) with anisotropic atomic displacement ellipsoids at 50% probability level. Hydrogen atoms were omitted for clarity. Selected bond lengths [Å] and angles [° ]: F1-B1=1.4164(12); F2-B1=1.4076(12); 01-C15=1.4122(12); O1-B1=1.4624(13); N1-C6=1.4864(11); C15-O1-B1=118.62(8); F2-B1-F1=107.04(8); F2-B1–01=110.69(8); F1-B1-O1=109.12(8); F2-B1-C1=109.67(8); F1-B1-C1=109.85(8); O1-B1-C1=110.40(7); C6-C1-B1=128.32(8); C2-C1-B1=115.97(7); C5-C6-N1=120.33(8); C1-C6-N1=117.12(7).

DETAILED DESCRIPTION

Glossary

In order to provide a clear and consistent understanding of the terms used in the present disclosure, a number of definitions are provided below. Moreover, unless defined otherwise, all technical and scientific terms as used herein have the same meaning as commonly understood by one of ordinary skill in the art to which this disclosure pertains.

The word "a" or "an" when used in conjunction with the term "comprising", "having", "including", or "containing" in the claims and/or the disclosure may mean "one", but it is also consistent with the meaning of "one or more", "at least one", and "one or more than one" unless the content clearly dictates otherwise. Similarly, the word "another" may mean at least a second or more unless the content clearly dictates otherwise.

As used in this disclosure and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

As used in this disclosure and claim(s), the word "consisting" and its derivatives, are intended to be close ended terms that specify the presence of stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The terms "about", "substantially" and "approximately" as used herein mean a reasonable amount of deviation of the modified term such that the end result is not significantly changed. These terms of degree should be construed as including a deviation of at least ±+1% of the modified term if this deviation would not negate the meaning of the word it modifies.

The present description refers to a number of chemical terms and abbreviations used by those skilled in the art. Nevertheless, definitions of selected terms are provided for clarity and consistency.

Abbreviations: NMR: Nuclear Magnetic Resonance; MS: Mass Spectrometry; m.p.:

melting point; HRMS: High Resolution Mass Spectrometry; ICP-MS: Inductively Coupled Plasma Mass Spectrometry; SEC: Size-Exclusion Chromatography; TMS: Tetramethylsilane; EtOAc: Ethyl Acetate; $CH_2Cl_2$: Dichloromethane (DCM); $CDCl_3$: Chloroform-d; AcOH: Acetic acid; TLC: Thin Layer Chromatography; FCC: Flash Column Chromatography; TMP=2,2,6,6-tetramethylpiperidine; TIPS: triisopropylsilyl.

As used herein, the term "alkyl" refers to straight-chain or branched-chain alkyl residues. This also applies if they carry substituents or occur as substituents on other residues, for example in alkoxy residues, alkoxycarbonyl residues or arylalkyl residues. Substituted alkyl residues are substituted in any suitable position. Examples of alkyl residues containing from 1 to 18 carbon atoms are methyl, ethyl, propyl, butyl, pentyl, hexyl, heptyl, octyl, nonyl, decyl, undecyl, dodecyl, tetradecyl, hexadecyl and octadecyl, the n-isomers of all these residues, isopropyl, isobutyl, isopentyl, neopentyl, isohexyl, isodecyl, 3-methylpentyl, 2,3,4-trimethylhexyl, sec-butyl, tert-butyl, or tert-pentyl. A specific group of alkyl residues is formed by the residues methyl, ethyl, n-propyl, isopropyl, n-butyl, isobutyl, sec-butyl and tert-butyl.

As used herein, the term "lower alkyl" refers to straight-chain or branched alkyl residues comprising 1 to 6 carbon atoms. This also applies if they carry substituents or occur as substituents on other residues, for example in alkoxy residues, alkoxycarbonyl residues or arylalkyl residues. Substituted alkyl residues can be substituted in any suitable position. Examples of lower alkyl residues containing from 1 to 6 carbon atoms are methyl, ethyl, propyl, isopropyl, butyl, isobutyl, tert-butyl, pentyl, isopentyl, neopentyl, and hexyl.

As used herein, the term "alkyloxy" is understood as being an "alkyl" bonded to an oxygen atom, non-limiting examples of which include methoxy, ethoxy, propoxy, iso-propoxy, n-butoxy, isobutoxy, t-butoxy and the like.

As used herein, the term "alkylthio" is understood as being an "alkyl" bonded to a sulfur atom, non-limiting examples of which include methylthio, ethylthio, propylthio, iso-propylthio, n-butylthio, iso-butylthio, sec-butylthio or tert-butylthio and the like.

As used herein, the term "cycloalkyl" is understood as being a monocyclic, bicyclic or polycyclic carbon-based ring system, non-limiting examples of which include cyclopropyl, cyclobutyl, cyclopentyl and cyclohexyl. Bicyclic or polycyclic carbon-based ring system can be fused, bridged and/or simply linked via a single bond.

As used herein, the term "arene" is understood as being an aromatic radical which is a single ring or multiple rings fused together and which is optionally substituted. When formed of multiple rings, at least one of the constituent rings is aromatic. Non-limiting examples of arenes include, phenyl, naphthyl and anthracenyl. The terms "arene" and "aryl" may be used interchangeably herein.

The term "heteroarene" as used herein embraces fully unsaturated or aromatic heterocyclo radicals. The heteroarene groups are either monocyclic, bicyclic, tricyclic or quadracyclic, provided they have a suitable number of atoms, for example from 3 to 30 atoms, and are stable. A bicyclic, tricyclic or quadracyclic heteroaryl group is fused, bridged and/or simply linked via a single bond. Examples of heteroarene groups include unsaturated 3 to 6 membered heteromonocyclic groups containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.; unsaturated condensed heterocyclo groups containing 1 to 5 nitrogen, oxygen and/or sulfur atoms including, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic groups containing an oxygen atom, including, for example, pyranyl, furyl, etc.; unsaturated 3 to 6-membered heteromonocyclic groups containing a sulfur or a selenium atom, including for example, thienyl, selenophen-yl, etc.; unsaturated 3- to 6-membered heteromonocyclic groups containing 1 to 2 oxygen atoms and 1 to 3 nitrogen atoms, including, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclo groups containing 1 to 2 oxygen atoms and 1 to 3 nitrogen atoms (e.g. benzoxazolyl, benzoxadiazolyl, etc.); unsaturated 3 to 6-membered heteromonocyclic: groups containing 1 to 2 sulfur atoms and 1 to 3 nitrogen atoms, including, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclo groups containing 1 to 2 sulfur atoms and 1 to 3 nitrogen atoms (e.g., benzothiazolyl, benzothiadiazolyl, etc.), unsaturated linked 5 or 6-membered heteromonocyclic groups containing 1 to 2 sulfur atoms and/or 1 to 3 nitrogen atoms, including, for example, bithienyl and trithienyl and the like. The term also embraces groups where heterocyclo groups are fused with aryl groups. Examples of such fused bicyclic groups include benzofuran, benzothiophene, benzopyran, and the like. The terms "heteroarene" and "heteroaryl" may be used interchangeably herein.

The term "substituted" as used herein, means that a hydrogen radical of the designated moiety is replaced with the group (radical) of a specified substituent, provided that the substitution results in a stable or chemically feasible compound. Non-limiting examples of substituents include halogen (F, Cl, Br, or I) for example F, and $C_{1-4}$alkyl.

The term "suitable" as used herein means that the selection of the particular compound and/or reagent and/or precatalyst and/or functionalization reagent and/or conditions would depend on the specific synthetic manipulation to be performed, and the identity of the molecule(s) to be transformed, but the selection would be well within the skill of a person trained in the art. All process/method steps described herein are to be conducted under conditions sufficient to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

As used herein, the term "derivative" refers to a structural analog and designates a compound having a structure similar to that of another one, but differing from it in respect of a certain component. It can differ in one or more atoms, functional groups, or substructures, which are replaced with other atoms, groups, or substructures. A structural analog can be imagined to be formed, at least theoretically, from the other compound. Despite a high chemical similarity, structural analogs are not necessarily functional analogs and can have very different physical, chemical, biochemical, or pharmacological properties.

As used herein, the term "precatalyst" refers to a catalyst in a stable salt form which does not itself act as a catalyst but which will form an active catalyst in situ.

The expression "proceed to a sufficient extent" as used herein with reference to the reactions or process steps disclosed herein means that the reactions or process steps proceed to an extent that conversion of the starting material or substrate to product is maximized. Conversion may be maximized when greater than about 5, 10, 15, 20, 25, 30, 35, 40, 45, 50, 55, 60, 65, 70, 75, 80, 85, 90, 95 or 99% of the starting material or substrate is converted to product.

As used herein, the term "protecting group" refers to well-known functional groups which, when bound to a functional group, render the resulting protected functional group inert to the reaction to be conducted on other portions of the compound and the corresponding reaction conditions, and which, at the appropriate time, can be reacted to regenerate the original functionality under deprotection conditions. The identity of the protecting group is not critical and is selected to be compatible with the remainder of the molecule. The conditions for bonding and removal of the protecting group are compatible with the remaining parts of the molecule. Commonly used protecting groups are disclosed in Greene, "Protective Groups In Organic Synthesis, $3^{rd}$ Edition" (John Wiley & Sons, New York, 1999), which is incorporated herein by reference.

The term "organoborane reagent" as used in the present disclosure refers to an organic derivative of borane ($BH_3$) and which is a source of boron in a reaction.

The term "frustrated Lewis pair" as used in the present disclosure refers to a compound or reagent containing a Lewis acid and a Lewis base which, because of steric hindrance or geometric constraints, cannot combine to form a strongly bound adduct, or may not in fact form any adduct at all.

As used herein, the term "Lewis acid" refers to an electron pair acceptor.

As used herein, the term "Lewis base" refers to an electron pair donor.

The term HBPin as used herein refers to pinacolborane.

The term BBN as used herein refers to 9-borabicyclo[3.3.1]nonane.

As used herein, the term "functionalization reagent" refers to a reagent that operates to functionalize a $sp^2$—H bond when used in the metal-free catalytic process of the present disclosure. In a non-limiting embodiment of the present disclosure, the functionalization reagent is an organoborane reagent. In yet further non-limiting embodiments of the present disclosure, functionalization reagents include, HBPin, HBCat and 9-BBN. Carbon hydrogen bond functionalization (C—H functionalization) is a type of reaction in which a C—H bond is cleaved and replaced by a C—X bond. In an embodiment of the present disclosure, the C—X bond can be a C—B bond (e.g. B is a boron atom). Carbon hydrogen bond functionalization usually implies that a catalyst is involved in the C—H cleavage process and typically comprises a first step that can be described as a C—H activation step.

As used herein, the term "functionalized" refers to the replacement of the hydrogen of a $sp^2$—H bond with the functionalization reagent residue. The functionalized residue obtained following functionalization of a $sp^2$—H bond may subsequently serve as a substrate for further chemical transformations. It is well within the purview of the skilled artisan to determine such further chemical transformations based of a particular functionalized residue.

As used herein, the expression "under conditions to provide a substrate comprising a functionalized $sp^2$ carbon" refers to the reaction conditions used to effect the functionalization of a substrate comprising a $sp^2$ carbon in the presence of a precatalyst and a functionalization reagent as described herein. In an embodiment, these conditions comprise, consist of or consist essentially of the combining of the substrate comprising a $sp^2$ carbon, a precatalyst and a functionalization reagent under an inert atmosphere and optionally with an inert solvent, followed by heating. In an embodiment, the substrate comprising a $sp^2$ carbon, the precatalyst and the functionalization reagent are heated to a temperature of about 50° C. to about 100° C., or about 60° C. to about 90° C., or about 70° C. to about 80° C. In an embodiment, the substrate comprising a $sp^2$ carbon, the precatalyst and the functionalization reagent are dissolved in chloroform.

Heating temperatures will vary depending on the reactants, however, will generally be about 50° C. to about 100° C., or about 60° C. to about 90° C., or about 70° C. to about 80° C. Reaction times will also vary depending on the reactants, but can be determined using methods known in the art, for example, by following the reaction progress by thin layer chromatography (TLC) or nuclear magnetic resonance (NMR) spectroscopy, and monitoring the disappearance of starting materials and/or formation of product. Reactions will be complete when a sufficient amount of the product is formed. Reaction solvents, temperatures and times are parameters that are readily selected by a person of skill in the art.

In an aspect, the present disclosure relates to precatalysts and processes for the metal-free functionalization of $sp^2$ carbons. In a further aspect, the present disclosure relates to precatalysts and processes for the metal-free borylation of sp² carbons. More specifically, but not exclusively, the present disclosure relates to precatalysts and processes for forming borylated alkenes, arenes and heteroarenes. In an embodiment of the present disclosure, the precatalysts for the borylation of sp² carbons include protected intramolecular FLPs. In an embodiment, such FLPs, when deprotected, can be used as catalysts in metal-free catalytic systems for $C_{sp2}$—H bond cleavage and dehydrogenative borylation of alkenes, arenes and heteroarenes. In a further embodiment of the present disclosure, the protected intramolecular FLPs are fluoroborate salts of the corresponding FLPs.

It was surmised that in the design of FLPs suitable for the metal-free activation of a $C_{sp2}$-H bond, systems that comprise a small Lewis acidic $BH_2$ moiety would allow for the alkylene, aryl or heteroaryl group to be borylated to come into proximity of the boron atom and would stabilize the generated alkylene, aryl or heteroaryl fragment while the presence of a basic moiety with steric bulk would facilitate the abstraction of the hydrogen atom from the $C_{sp2}$ of the alkylene, aryl or heteroaryl group and prevent possible head-to-tail dimerization. In an embodiment of the present disclosure, the basic moiety can be an amino-moiety. Non limiting examples of amino moieties include —$NR_1R_2$ wherein $R_1$ and $R_2$ are independently selected from $C_{1-15}$alkyl. In a further embodiment, $R_1$ and $R_2$ are independently selected from $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl, $C_{10}$-alkyl, $C_{11}$-alkyl, $C_{12}$-alkyl, $C_{13}$-alkyl, $C_{14}$-alkyl and $C_{15}$-alkyl. In a further embodiment, $R_1$ and $R_2$ are independently selected from $C_{1-5}$-alkyl. In a further embodiment, $R^1$ and $R_2$ are independently selected from substituted $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl, $C_{10}$-alkyl, $C_{11}$-alkyl, $C_{12}$-alkyl, $C_{13}$-alkyl, $C_{14}$-alkyl and $C_{15}$-alkyl. In a further embodiment, $R^1$ and $R^2$ may be connected together to form a nitrogen containing ring system that may optionally be substituted by 1, 2, 3, 4, 5, or 6 substituents. In a further embodiment, the precatalysts of the present disclosure comprise an arene linker.

2-TMP-phenyl boronic acid (2) is prepared in good yields from 2-TMP-iodobenzene by the successive addition of n-butyllithium and of three equivalents of $B(OMe)_3$, followed by hydrolysis (Scheme 1).

Scheme 1

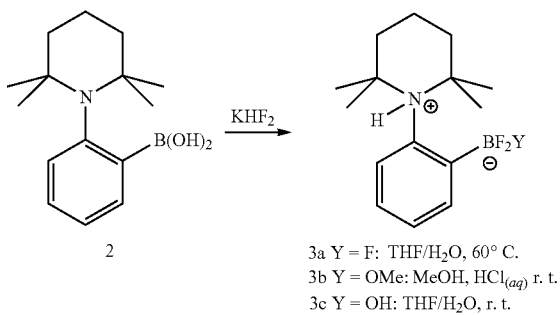

2

3a Y = F: THF/H₂O, 60° C.
3b Y = OMe: MeOH, HCl$_{(aq)}$ r. t.
3c Y = OH: THF/H₂O, r. t.

Interestingly, the subsequent reaction of 2 with $KHF_2$ affords different salts depending on the reaction conditions, with 1-trifluoroborato-2-TMPH-benzene (3a) being the thermodynamic end product in all cases, as determined by density functional theory (DFT). 1-(Difluoromethoxyborato)-2-TMPH-benzene (3b) is isolated in excellent yield by reacting 2 and $KHF_2$ in methanol at room temperature over a period of one hour. However, in a tetrahydrofuran-water mixture, 1-(difluorohydroxyborato)-2-TMPH-benzene (3c) is obtained after 25 minutes, while 3a is the main products if longer reaction times or higher temperatures are used. The synthesis and storage of all three products is convenient and does not require any special considerations.

All three compounds (3a-c) are unambiguously characterized by NMR spectroscopy. In their ¹¹B {¹H} NMR spectra, difluoroborate species 3b and 3c are recognizable by triplet signals at about δ=3.4 and about δ=3.5 respectively, while 3a displays a quadruplet resonance at about δ=3.2, owing to the coupling of the boron atom with the three fluorine-19 atoms. The solid state structures of these compounds (3a-c) is also confirmed by X-ray diffraction (XRD); the ORTEP (Oak Ridge Thermal Ellipsoid Plot) representation of compounds 3a-c is illustrated in FIGS. 2-4.

In an embodiment of the present disclosure, the utility of compounds 3a-c as precatalysts for the dehydrogenative borylation of heteroarenes was investigated. Trifluoroborate salt 3a is shown to reacts slowly with five equivalents of HBPin in $CDCl_3$ to give a mixture of products within five hours at 80° C. Similarly, difluoro(methoxy)borate 3b reacts with HBPin in 90 minutes at 80° C. While the reaction mixtures proved somewhat difficult to analyze, in both cases $H_2$ release could be observed by ¹H NMR analysis. Moreover, a broad peak at about δ=150.8 was the main resonance in the ¹⁹F NMR spectra and was associated to fluoropinacolborane. When 3b was exposed to 20 equivalents of HBPin in $CDCl_3$, broad peaks (at about δ=5.2 and 2.3) could be observed by ¹H NMR and a singlet could be observed at about δ=20.4 by ¹¹B NMR, typical of the B—H bonds in 1-TMP-2-borylbenzene, confirming the conversion of 3b to catalytically relevant 1-TMP-2-borylbenzene.

Ligand scrambling at boron and formation of 3a from 3b is also observed in the presence of HBPin. This scrambling could not be observed when pure samples of 3b are heated in $CDCl_3$, but could be catalyzed by the addition of traces of Lewis acidic $B(C_6F_5)_3$ suggesting that electrophilic abstraction of ligands from 3a-c is possible with hydroboranes.

These results suggest that fluoroborate salts 3a-c can be conveniently deprotected (i.e. converted to the catalytically relevant $BH_2$ derivative 1-TMP-2-borylbenzene) under the same reaction conditions as those that are used for the metal-free borylation of alkenes, arenes and heteroarenes. Fluoroborate salts 3a-c can thus be used directly as precatalysts for the borylation of alkenes, arenes and heteroarenes.

A general procedure for the metal-free borylation of heteroarenes in accordance with an embodiment of the present disclosure is illustrated hereinbelow in Scheme 2.

Scheme 2

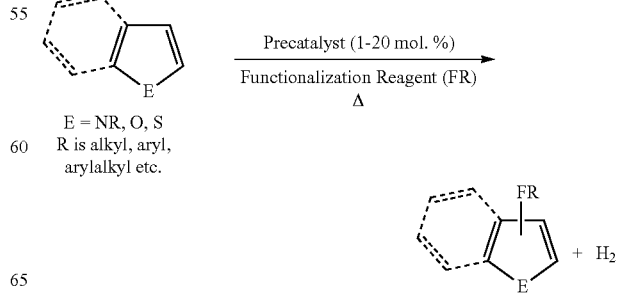

E = NR, O, S
R is alkyl, aryl, arylalkyl etc.

A general procedure for the metal-free borylation of heteroarenes in accordance with a further embodiment of the present disclosure is illustrated hereinbelow in Scheme 3.

Scheme 3

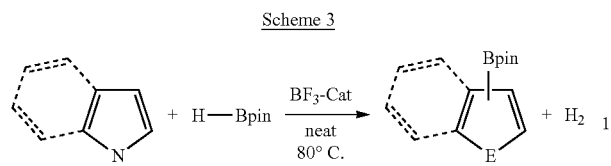

A general procedure for the metal-free borylation of heteroarenes in accordance with a further embodiment of the present disclosure is illustrated hereinbelow in Scheme 4.

Scheme 4

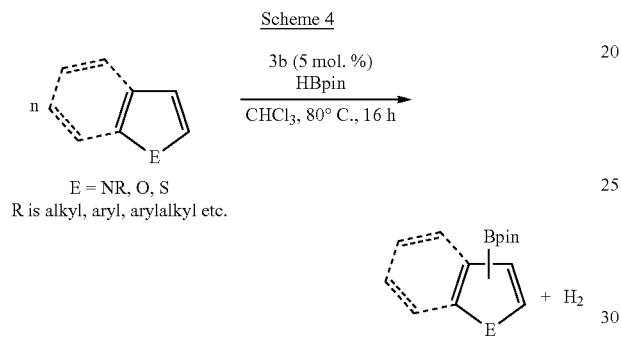

E = NR, O, S
R is alkyl, aryl, arylalkyl etc.

In an embodiment of the present disclosure, fluoroborate salts 3a-c are used directly as precatalysts for the borylation of 1-methylpyrrole, using HBPin as the borylating reagent (functionalization reagent). $^1$H NMR monitoring of the reaction of HBPin with 1-methylpyrrole in the presence of 1-TMP-2-borylbenzene or 3a-c over several hours, allowed for the conversion of 1-methylpyrrole to 1-methyl-2-(BPin) pyrrole to be observed in all cases (FIG. 1). Interestingly, the reaction profile features an induction period when fluoroborate salts 3a-c are used, confirming that these species act as precatalysts and require deprotection in order to generate the active (catalytically relevant) 1-TMP-2-borylbenzene species. HBPin was used directly as obtained from commercial sources. Neither purification of the borane by distillation, nor addition of B(C$_6$F5)$_3$ (0.5 mol. %) had any significant effect on the kinetics of the catalytic reactions. It would thus appear that the deprotection of the precatalysts is not mediated by Lewis acidic impurities present in HBPin. In an embodiment of the present disclosure, the fluoroborate salts were used directly as precatalysts for the borylation of a variety of different heteroarene substrates, non-limiting examples of which include 1-benzylpyrrole, 1-benzylindole, 1-methylpyrrole, 1,2-dimethylindole, 1-(tert-butyldimethylsilyl)-1H-indole, 2-tert-butylfuran, 2-(trimethylsiloxy)furan, N-(tert-butyldimethylsilyl)-7-azaindole, 3,4-ethylenedioxythiophene and 1-methylindole, using HBPin as the borylating reagent. In a further embodiment of the present disclosure, the catalytic reactions were performed in simple sealable vials, under normal conditions (e.g. standard anhydrous benchtop techniques), using precatalysts that were stored on the bench for several weeks prior to use. In yet a further embodiment of the present disclosure, the catalytic reactions were performed without the use of a glovebox or of a Schlenk apparatus.

In an embodiment of the present disclosure, the borylation of a variety of different substrates, non-limiting examples of which include 1-methylpyrrole, 1-benzylpyrrole, 2-tert-butylfuran, 2-(trimethylsiloxy)furan 3,4-ethylenedioxythiophene and 1-methylindole, was performed using fluoroborate salt 3b as the precatalyst and HBPin as the borylating reagent (Table 1). High yields were obtained in all cases, reflecting the reactivity previously observed using the catalytically relevant 1-TMP-2-borylbenzene species, while performing the borylation reactions under standard anhydrous benchtop techniques.

TABLE 1

Catalytic results for the borylation of heteroaromatic substrates using precatalyst 3b and functionalization reagent HBpin.

| Product | n | Yield (%) |
|---|---|---|
| ![pyrrole Bpin 88:11] | 1 | 85 |
| ![benzylpyrrole Bpin 3:2] | 2 | 78 |
| TMSO-furan-Bpin | 2 | 94 |
| tBu-furan-Bpin | 0.67 | 70 |
| EDOT-Bpin | 2 | 96 |
| indole-Bpin | 2 | 81 |

Conditions: 3b (10 mg, 0.034 mmol, 5 mol. %), HBPin (99.0 mg, 112 μL 0.774 mmol, 23 eq.), and substrate (n × 0.673 mmol, n × 20 eq.) in 1.6 mL of CHCl$_3$ at 80° C.
The yields are given with respect to the transformation of 20 eq. of HBPin, (3 eq. being consumed for the deprotection of the catalyst) as measured by $^1$H NMR spectroscopy at the end of the reaction. Yields and isomer ratios refer to isolated quantities.

EXPERIMENTAL

In accordance with various embodiments of the present disclosure, a number of examples are provided hereinbelow illustrating the borylation of various substrates using the fluoroborate salts as described herein. The following non-limiting examples are illustrative of the present disclosure.

Materials

Chemicals: Toluene and hexanes used in the synthesis of 2 were purified by distillation over Na/benzophenone. Chloroform used in the catalytic reactions was dried by distillation over $P_2O_5$. $CDCl_3$ used for the kinetic catalytic reactions and deprotection investigations was similarly treated. $CDCl_3$ used for product and precatalyst characterization was used as received from Sigma-Aldrich. $C_6D_6$ was dried over Na/K alloy and distilled. $Al_2O_3$ was purchased from Sigma-Aldrich and activated by heating in a Schlenk flask at 300° C. under vacuum (20 millitorr) for 16 hours. Heteroaromatic substrates were purchased from Sigma-Aldrich. 1-Methylpyrrole was distilled from KOH and flame-dried $MgSO_4$. 2-tButylfuran, 3,4-ethylenedioxythiophene and 1-methylindole were used as received. 1-Benzylpyrrole was passed through a short pad of alumina before use. Pinacolborane was purchased from Sigma-Aldrich and used as received. 2-TMP-iodobenzene was synthesized according to a reported literature procedure.[52]

Instrumentation/Characterization: NMR spectra were recorded on an Agilent Technologies NMR spectrometer at 500 MHz ($^1$H), 125.758 MHz ($^{13}$C), 160.46 MHz ($^{11}$B) and on a Varian Inova NMR AS400 spectrometer, at 400.0 MHz ($^1$H), 100.580 MHz ($^{13}$C). $^1$H NMR and $^{13}$C{$^1$H} NMR chemical shifts were referenced to residual protons or carbons in deuterated solvent. $^{11}$B{$^1$H} was calibrated using an external $BF_3.Et_2O$ reference. Multiplicities were reported as singlet (s), broad singlet (s, br) doublet (d), triplet (t) or multiplet (m). Chemical shifts were reported in ppm. Coupling constants were reported in Hz. Mass Spectrometry analyses were carried out on an Agilent Technologies 6210 LC Time of Flight Mass Spectrometer. Gas chromatography was carried out on a Thermo-Fisher Trace GC Ultra with an ITQ 900 MS, using electronic impact as an ionization source (precision+/−0.2 uma).

Synthesis of Precatalysts (2-TMP-Benzene) Boronic Acid (2)

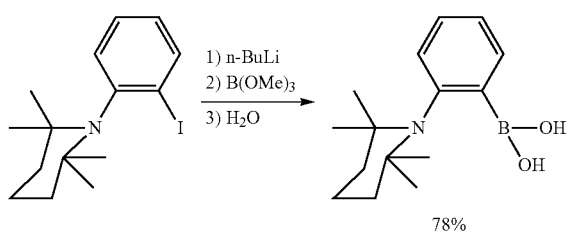 [SMILES: CC1(C)CCCC(C)(C)N1c1ccccc1I ; CC1(C)CCCC(C)(C)N1c1ccccc1B(O)O]

78%

2-TMP-iodobenzene (4.3 g, 12.5 mmol) was dissolved in ca. 40 mL of dry hexanes and n-BuLi (5 mL of a 2.5 M solution in hexanes, 1 eq.) was added at −78° C. The reaction mixture was left warming while stirring for approximately 4 h until it reached room temperature and a white precipitate formed. The solvent was removed and ca. 40 mL of toluene was added. The reaction mixture was then cooled to −78° C. followed by the addition of 3 equivalents of $B(OMe)_3$ (4.3 mL). The reaction was left to warm to room temperature and stirred overnight (ca. 16 h). The next morning, water (ca. 40 mL) was added and the mixture was stirred for an additional 3 h. The reaction mixture was then extracted three times with $CHCl_3$ and the combined organic fractions were dried with $MgSO_4$. A white powder (3.03 g) was obtained after evaporation that was subsequently identified by $^1$HNMR as a methanol adduct of the target compound.

Trituration of the solid in water (50 mL) and evaporation under vacuum at 50° C. gave the target compound as a white powder (2.54 g, 78% yield). A suitable single crystal for XRD was obtained by slow evaporation of an acetone solution at room temperature.

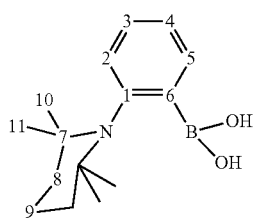

$^1$H-NMR 500 MHz: δ 9.05 (s, broad, 2H, OH); 7.98 (d, $^3J_{H-H}$=7 Hz, 1H, H2 or H5); 7.44-7.37 (m, 2H, H3 or H4 and H2 or H5); 7.29 (t, $^3J_{H-H}$=7 Hz, 1H, H3 or H4); 2.02-1.90 (m, 1H, H9); 1.81-1.66 (m, 5H, H8 and H9); 1.43 (s, 6H, H10 or H11); 0.88 (s, 6H, H10 or H11). $^{13}$C {$^1$H} (126 MHz): δ 151.5 (s, 1C, C1); 135.1, 130.3, 129.4, 126.0 (s, 4C, C2, C3, C4 and C5); 56.7 (s, 2C, C7); 41.7 (s, 2C, C8); 32.0 (s, 2C, C10 or C11); 25.0 (s, 2C, C10 or C11); 18.1 (s, 1C, C9). C6 was not observed. $^{11}$B {$^1$H} (160 MHz): δ 29.8 (s, 1B). Elemental analysis calculated for $C_{15}H_{24}B_1N_1O_2$: C, 68.98%; H, 9.26%; N, 5.36%; Found: C, 68.97%; H, 9.30%; N, 5.36%. [M+H]$^+$=262.2115 (calc.: 262.19785).

1-(Trifluoroborato)-2-TMP-benzene (3a)

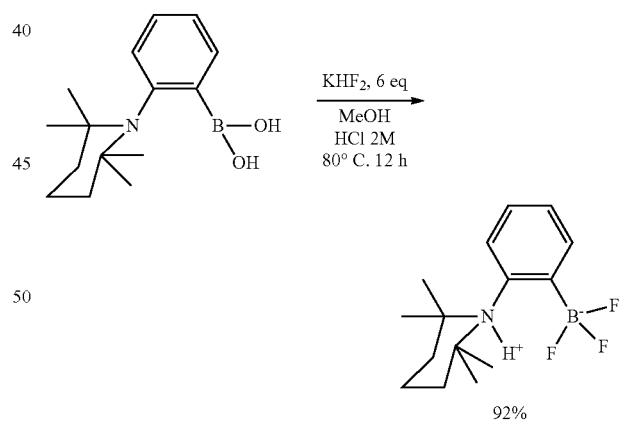

To a solution of 2 (250 mg, 0.95 mmol) in methanol (10 mL), were added $KHF_2$ (445 mg, 5.7 mmol) and 1 mL of a 2M HCl solution in water. The reaction mixture was sonicated for 30 minutes and stirred at 80° C. for 12 h. After evaporation of the volatiles in vacuo, a white solid was obtained that was subsequently extracted three times with $CHCl_3$. The combined organic fractions were dried to yield the target compound (250 mg, 92% yield).

A suitable single crystal for XRD was obtained by slow evaporation of an acetone solution at room temperature.

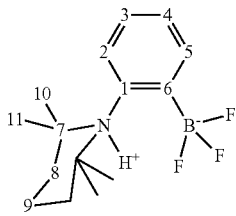

¹H-NMR 500 MHz: δ 9.7 (d, broad, J=12 Hz, 1H, NH); 7.81 (d, ³J$_{H-H}$=7 Hz, 1H, H2 or H5); 7.41 (t, ³J$_{H-H}$=7 Hz, 1H, H2 or H5); 7.32-7.22 (m, 2H, H3 or H4 and H2 or H5); 2.04-1.95 (m, 5H, H8 and H9); 1.89-1.83 (m, 1H, H9); 1.65 (s, 6H, H10 or H11); 1.22 (s, 6H, H10 or H11). ¹³C {¹H} (126 MHz): δ 136.6 (s, 1C, C1); 135.5, 129.2, 127.0, 121.1 (s, 4C, C2, C3, C4 and C5); 67.8 (s, 1C, C7); 39.6 (s, 2C, C8); 30.3 (s, 2C, C10 or C11); 23.5 (s, 2C, C10 or C11); 16.5 (s, 1C, C9). ¹⁹F {¹H} (470 MHz): δ −134.0 (m). 11B {¹H} (160 MHz): δ 3.3 (m). Elemental analysis calculated for C15H23B1N1F3: C, 63.18%; H, 8.13%; N, 4.91%; Found: C, 63.02%; H, 8.67%; N, 4.98%. [M−H]⁻=284.1810 (calc.: 284.1797).

1-(Difluoromethoxyborato)-2-TMP-benzene (3b)

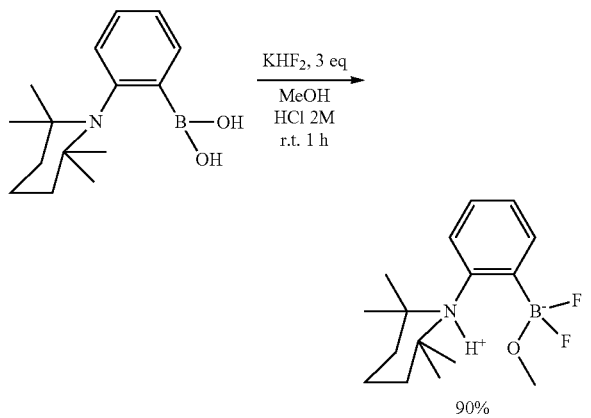

To solution of 2 (500 mg, 1.91 mmol) in methanol (10 mL), were added KHF₂ (445 mg, 5.7 mmol) and 1 mL of a 2M HCl solution in water. The reaction mixture was sonicated for 5 minutes and stirred at room temperature for one hour. After evaporation of the volatiles in vacuo, a white solid was obtained that was subsequently extracted three times with CHCl₃. The combined organic fractions were dried and evaporated to yield the target compound (514 mg, 90% yield).

A suitable single crystal for XRD was obtained from a saturated toluene solution at −35° C.

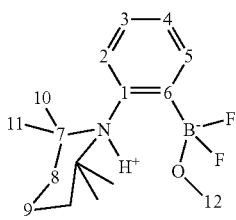

¹H-NMR 500 MHz: δ 13.0 (s, broad, 1H, NH); 7.83 (d, ³J$_{H-H}$=7 Hz, 1H, H2 or H5); 7.37 (t, ³J$_{H-H}$=7 Hz, 1H, H2 or H5); 7.24-7.16 (m, 2H, H3 or H4 and H2 or H5); 3.58 (s, 3H, H12); 2.03-1.87 (m, 6H, H8 and H9); 1.60 (s, 6H, H10 or H11); 1.17 (s, 6H, H10 or H11). ¹³C {¹H}(126 MHz): δ 137.7 (t, ³J$_{C-F}$=4 Hz, 1C, C1); 137.7, 135.2, 128.8, 121.4 (s, 4C, C2, C3, C4 and C5); 65.5 (s, 1C, C7); 47.1 (t, ³J$_{C-F}$=5 Hz, 2C, C12); 39.5 (s, 2C, C8); 29.8 (s, 2C, C10 or C11); 23.8 (s, 2C, C10 or C11); 16.8 (s, 1C, C9).¹⁹F {¹H} (470 MHz): δ −147.8 (q, ¹J$_{F-B}$=58 Hz). ¹¹B {¹H} (160 MHz): δ 3.4 (t, ¹J$_{B-F}$=59 Hz). Elemental analysis calculated for C16H26B1N1F2O1: C, 64.66%; H, 8.82%; N, 4.71%; Found: C, 64.31%; H, 9.21%; N, 4.79%. [M−H]⁻=296.2018 (calc.: 296.1997).

1-(Difluorohydroxyborato)-2-TMP-benzene (3c)

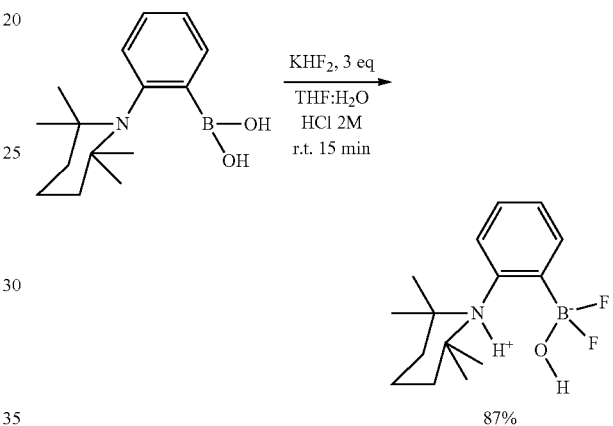

To solution of 2 (500 mg, 1.91 mmol) in THF:H₂O (20 mL of a 5:1 mixture), was added KHF₂ (445 mg, 5.7 mmol). The reaction mixture was stirred at room temperature for 15 minutes and then extracted with CHCl₃ (3×15 mL). After evaporation of the volatiles in vacuo, the target compound was obtained as a white solid in 87% yield (470 mg).

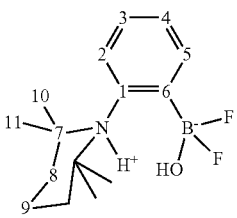

¹H-NMR 500 MHz: δ 12.6 (s, broad, 1H, NH); 7.89 (d, ³J$_{H-H}$=7 Hz, 1H, H2 or H5); 7.41 (t, ³J$_{H-H}$=7 Hz, 1H, H2 or H5); 7.26-7.21 (m, 2H, H3 or H4 and H2 or H5); 2.39 (s, broad, 1H, OH); 2.11-1.81 (m, 6H, H8 and H9); 1.65 (s, 6H, H10 or H11); 1.26 (s, 6H, H10 or H11). ¹³C {¹H} (126 MHz): δ 137.6 (t, J=4 Hz, 1C, C1); 135.4, 129.0, 126.4, 121.3 (s, 4C, C2, C3, C4 and C5); 66.2 (s, 1C, C7); 39.2 (s, 2C, C8); 30.0 (s, 2C, C10 or C11); 23.8 (s, 2C, C10 or C11); 16.8 (s, 1C, C9). ¹⁹F {¹H} (470 MHz): δ −133.9 (q, 1J$_{F-B}$=53 Hz). ¹¹B {¹H} (160 MHz): δ 3.5 (t, J$_{B-F}$=61 Hz). Elemental analysis calculated for C15H24B1N1F2O1: C, 63.62%; H, 8.54%; N, 4.95%; Found: C, 63.60%; H, 8.84%; N, 4.89%.

1-(Trifluoroborato)-2-piperidinyl-benzene (4a)

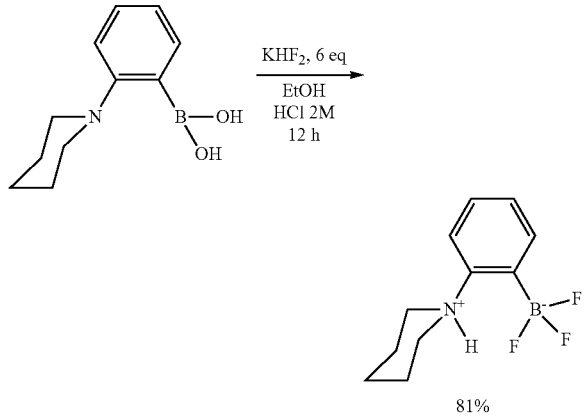

81%

To a solution of 2-(1-piperidinyl) phenyl boronic acid (6.0 g, 29.3 mmol) in ethanol (250 mL), were added KHF$_2$ (13.7 g, 175.6 mmol) and 32 mL of a 2M HCl solution in water. The reaction mixture was sonicated for 30 minutes and stirred at room temperature for 12 h. After evaporation of the volatiles in vacuo, the resulting white residue was extracted with chloroform (3×100 mL). The combined organic fractions were dried with MgSO$_4$ and evaporated to yield the target compound (5.4 g, 81% yield).

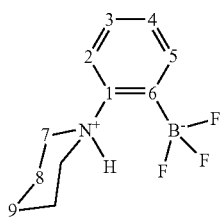

$^1$H-NMR 500 MHz: δ 9.25 (s, broad, 1H, NH); 7.77 (dd, $^3J_{H\text{-}H}$=7.3 Hz, 1H, H2); 7.39 (t, $^3J_{H\text{-}H}$=7.3 Hz, 1H, H3); 7.33 (td, 1H, $^3J_{H\text{-}H}$=8.0 Hz, H4); 7.24 (d, 1H, $^3J_{H\text{-}H}$=8.0 Hz, H5); 3.40 (m, 2H, H7); 3.67 (m, 2H, H7); 2.14 (m, 2H, H8); 2.03-1.92 (m, 3H, 2H of H8 and 1H of H9); 1.65 (m, 1H, H9). $^{13}$C{$^1$H} (126 MHz): δ 144.1 (s, 1C, C1); 134.8 (q, 1C, C5, $^3J_{C\text{-}F}$=1.9 Hz); 129.6, 128.5, 116.9 (s, 3C, C2, C3 and C4); 57.1 (s, 2C, C7); 24.9 (s, 2C, C8); 21.3 (s, 2C, C9). $^{19}$F{$^1$H} (470 MHz): δ −137.6 (m). $^{11}$B{$^1$H} (160 MHz): δ 3.1 (m).

1-(Trifluoroborato)-2-diethylamino-benzene (5a)

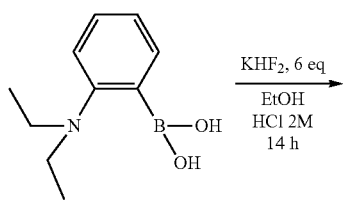

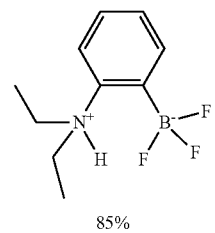

85%

To a solution of 2-(1-diethylamino) phenyl boronic acid (10.0 g, 51.8 mmol) in ethanol (500 mL), were added KHF$_2$ (24.2 g, 310.8 mmol) and 56 mL of a 2M HCl solution in water. The reaction mixture was sonicated for 30 minutes and stirred at room temperature for 14 h. After evaporation of the volatiles in vacuo, the residue was extracted with chloroform (3×100 mL). The combined organic fractions were dried with MgSO$_4$ and evaporated to yield the target compound (9.55 g, 85% yield).

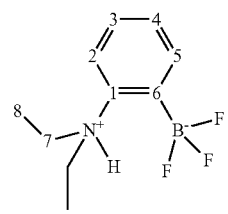

$^1$H-NMR 500 MHz: δ 9.19 (s, broad, 1H, NH); 7.82 (m, 1H, H2); 7.44-7.38 (m, 2H, H3 and H4); 7.16 (m, 1H, H5); 3.85 (m, 2H, H7); 3.46 (m, 2H, H7); 1.22 (t, $^3J_{H\text{-}H}$=7.2 Hz, 6H, H8). $^{13}$C{$^1$H} (126 MHz): δ 138.8 (s, 1C, C1); 134.8 (q, 1C, C5, $^3J_{C\text{-}F}$=1.9 Hz); 129.3, 128.9, 116.9 (s, 3C, C2, C3 and C4); 54.6 (s, 2C, C7); 10.5 (s, 2C, C8). $^{19}$F{$^1$H} (470 MHz): δ −135.6 (m). $^{11}$B{$^1$H} (160 MHz): δ 3.1 (m).

1-(Trifluoroborato)-2-dimethylamino-benzene (6a)

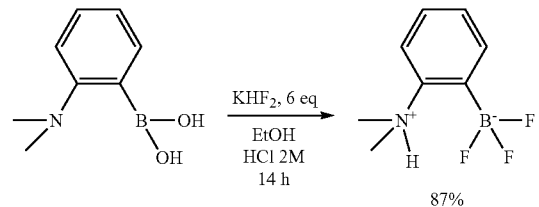

87%

To a solution of 2-(1-dimethylamino) phenyl boronic acid (1.5 g, 9.1 mmol) in ethanol (50 mL), were added KHF$_2$ (4.3 g, 54.5 mmol) and 10 mL of a 2M HCl solution in water. The reaction mixture was sonicated for 30 minutes and stirred at room temperature for 14 h. After evaporation of the volatiles in vacuo, the residue was extracted with chloroform (3×50 mL). The combined organic fractions were dried with MgSO$_4$ and evaporated to yield the target compound (1.49 g, 87% yield).

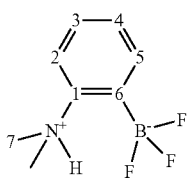

$^1$H-NMR 500 MHz: δ 9.57 (s, broad, 1H, NH); 7.82 (dd, $^3J_{H-H}$=6.8 Hz, 1H, H2); 7.45-7.39 (m, 2H, H3 and H4); 7.29 (m, 1H, H5); 3.40 (s, 3H, H7); 3.39 (m, 3H, H7). $^{13}$C{$^1$H} (126 MHz): δ 145.1 (s, 1C, C1); 134.7 (q, 1C, C5, $^3J_{C-F}$=2.5 Hz); 129.5, 128.7, 116.3 (s, 3C, C2, C3 and C4); 47.7 (s, 2C, C7). $^{19}$F{$^1$H} (470 MHz): δ −138.6 (m). $^{11}$B{$^1$H} (160 MHz): δ 3.1 (m).

General Method for the $^1$H NMR Monitoring of the Borylation Reactions.

In a glovebox, a solution of hexamethylbenzene (internal standard) and catalyst or precatalyst (1, 3a-c) (0.01 mmol) in CDCl$_3$ (0.4 mL) was prepared and introduced into a J-Young NMR tube. To this tube was subsequently added HBpin (28.3 μL, 14.9 mg, 0.195 mmol) and 1-methylpyrrole (18.3 μL, 15.8 mg, 0.195 mmol) by automatic syringe. The J-Young tube was inserted in a NMR spectrometer at 80° C. and $^1$H NMR spectra were acquired at intervals over a period of 12 hours, along with $^{19}$F NMR spectra. The yields were calculated according to the conversion of HBpin as measured against the internal standard.

Catalytic Borylation Reactions

General Procedure for the Catalytic Borylation of Heteroaromatic Substrates Under Neat Conditions in Accordance with an Embodiment of the Present Disclosure.

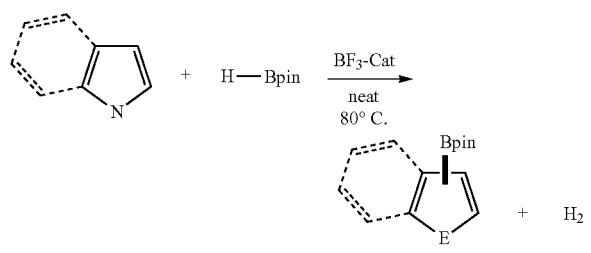

Precatalyst BF$_3$-Cat (10-20 mol %), substrate (0.5 mmol) and pinacolborane (1.3-2 eq.) were introduced into an oven-dried flask (10 mL) containing a magnetic stirring bar, connected to a condenser that is already connected to a nitrogen flow line. The reaction mixture was subsequent stirred for 2-20 hours at 80° C. in an oil bath. Samples were taken for NMR analysis using hexamethylbenzene as an internal standard and CDCl$_3$ as solvent.

Borylation of N-Benzylindole

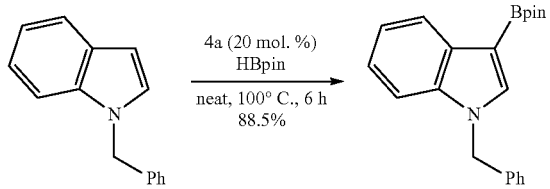

Quantities: N-benzylindole (104 mg, 0.5 mmol); pinacolborane (132 mg, 150 μL, 2 eq., 1 mmol); Catalyst 4a (22.9 mg, 0.1 mmol). $^1$H NMR conversion: 88.5%.

Borylation of 1,2-dimethylindole

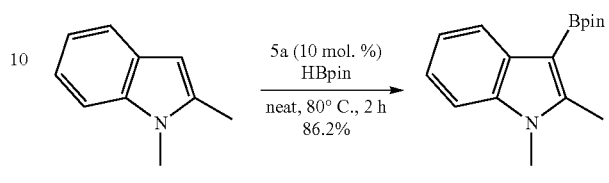

Quantities: 1,2-dimethylindole (73 mg, 0.5 mmol); pinacolborane (132 mg, 150 μL, 2 eq., 1 mmol); Catalyst 5a (10.9 mg, 0.05 mmol). $^1$H NMR conversion: 86.2%.

Borylation of 1-(tert-butyldimethylsilyl)-1H-indole

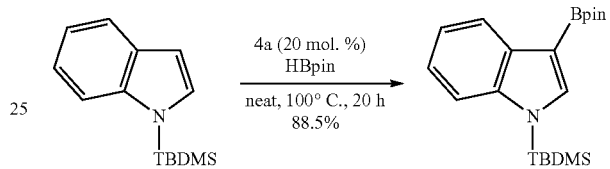

Quantities: 1-(tert-butyldimethylsilyl)-1H-indole (116 mg, 0.5 mmol); pinacolborane (132 mg, 150 μL, 2 eq., 1 mmol); Catalyst 4a 22.9 mg (0.1 mmol). $^1$H NMR conversion: 88.5%.

Borylation of N-(tert-butyldimethylsilyl)-7-azaindole

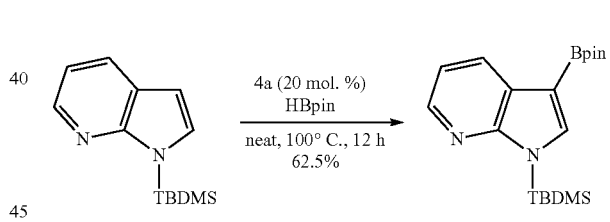

Quantities: N-(tert-butyldimethylsilyl)-7-azaindole (117 mg, 0.5 mmol); pinacolborane (132 mg, 150 μL, 2 eq., 1 mmol); Catalyst 4a (22.9 mg, 0.1 mmol). $^1$H NMR conversion: 62.5%.

General Procedure for the Catalytic Borylation of Heteroaromatic Substrates in Accordance with an Embodiment of the Present Disclosure.

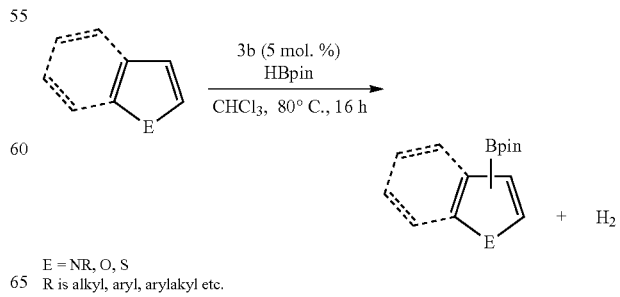

E = NR, O, S
R is alkyl, aryl, arylakyl etc.

Precatalyst 3b (10 mg, 0.034 mmol) was introduced into an oven-dried microwave vial (5 mL) containing a magnetic stirring bar, along with the heteroaromatic substrate. The vial was capped and purged with $N_2$ (through a needle) for at least 10 minutes before the addition of $CHCl_3$ (1.6 mL) via syringe and pinacolborane (23 eq., 99.0 mg, 112 μL) by microsyringe. At this point, the $N_2$ inlet was removed. The reaction mixture was then stirred for 16 hours in an oil bath kept at 80° C. The resulting mixture was subsequently filtered through a short pad of silica, which was rinsed with additional chloroform. The resulting filtrate was evaporated to complete dryness in vacuo to afford the desired product.

Borylation of 1-methylpyrrole

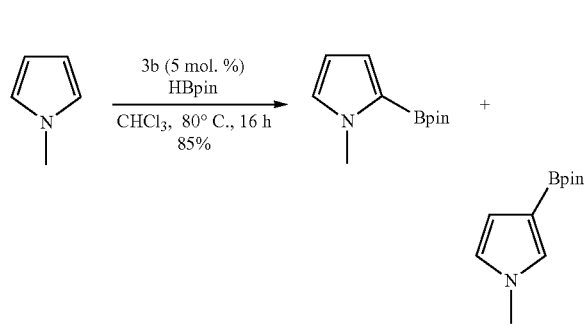

Quantity of 1-methylpyrrole: 60 μL (55 mg, 0.67 mmol, 1 eq.). Yield: 85% (119 mg) of a 89:11 mixture of 1-methyl-2-(4,4,5,5-tetramethyl-1,3,2-dioxaborolan-2-yl)pyrrole and 1-methyl-3-(4,4,5,5-tetramethyl-1,3,2-dioxaborolan-2-yl)pyrrole.

1-Methyl-2-(4,4,5,5-tetramethyl-1,3,2-dioxaborolan-2-yl)pyrrole: $^1$H NMR (400 MHz, $CDCl_3$): δ 6.81 (m, 2H), 6.15 (m, 1H), 3.84 (s, 3H), 1.31 (s, 12H); $^{13}C\{^1H\}$ NMR (101 MHz, $CDCl_3$): δ 128.3, 122.0, 108.6, 83.2, 36.7, 25.0; $^{11}B\{^1H\}$ NMR (160 MHz, $CDCl_3$): δ 28.1.1-Methyl-3-(4,4,5,5-tetramethyl-1,3,2-dioxaborolan-2-yl)pyrrole: $^1$H NMR (400 MHz, $CDCl_3$): δ 7.06 (m, 1H), 6.64 (m, 1H), 6.47 (m, 1H), 3.66 (s, 3H), 1.29 (s, 12H).

Borylation of 1-benzylpyrrole

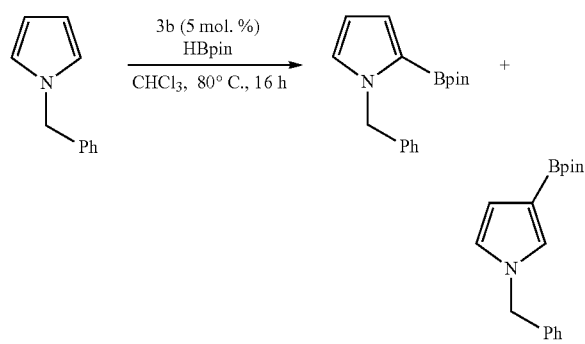

Quantity of 1-benzylpyrrole: 207 μL (211 mg, 1.35 mmol, 2 eq.). Yield: 78% of a 3:2 mixture of 1-benzyl-2-(4,4,5,5-tetramethyl-1,3,2-dioxaborolan-2-yl)pyrrole and 1-benzyl-3-(4,4,5,5-tetramethyl-1,3,2-dioxaborolan-2-yl)pyrrole.

1-Benzyl-2-(4,4,5,5-tetramethyl-1,3,2-dioxaborolan-2-yl)pyrrole: $^1$H NMR (400 MHz, $CDCl_3$): δ 7.30-7.17 (m, 3H), 7.12-7.06 (m, 2H), 6.89 (dd, J=2.4, 1.6 Hz, 1H), 6.86 (dt, J=3.6, 1.9 Hz, 1H), 6.23-6.19 (m, 1H), 5.39 (s, 2H), 1.24-1.21 (m, 13H). 1-Benzyl-3-(4,4,5,5-tetramethyl-1,3,2-dioxaborolan-2-yl)pyrrole: $^1$H NMR (400 MHz, $CDCl_3$): δ 7.36-7.26 (m, 3H), 7.17-7.12 (m, 3H), 6.73-6.68 (m, 1H), 6.51 (dd, J=2.6, 1.7 Hz, 1H), 5.06 (s, 2H), 1.31 (s, 12H); Mixture: $^{13}C\{^1H\}$ NMR (126 MHz, $CDCl_3$): δ 139.8, 137.7, 130.4, 128.9, 128.5, 127.9, 127.7, 127.5, 127.2, 127.0, 122.4, 122.3, 114.6, 109.1, 83.3, 82.9, 53.5, 52.9, 25.0, 24.8; $11B\{1H\}$ NMR (160 MHz, $CDCl_3$): δ 27.8.

Borylation of 1-methylindole

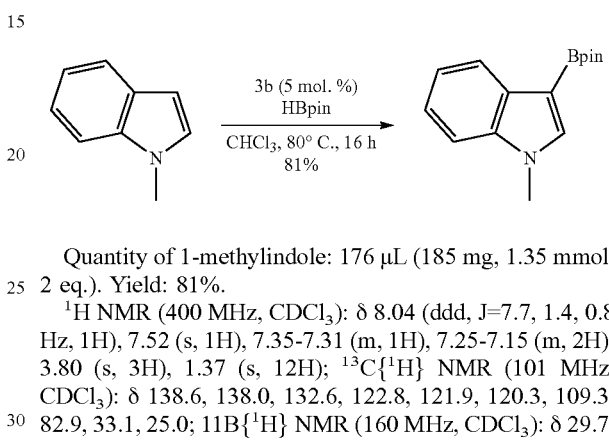

Quantity of 1-methylindole: 176 μL (185 mg, 1.35 mmol, 2 eq.). Yield: 81%.

$^1$H NMR (400 MHz, $CDCl_3$): δ 8.04 (ddd, J=7.7, 1.4, 0.8 Hz, 1H), 7.52 (s, 1H), 7.35-7.31 (m, 1H), 7.25-7.15 (m, 2H), 3.80 (s, 3H), 1.37 (s, 12H); $^{13}C\{^1H\}$ NMR (101 MHz, $CDCl_3$): δ 138.6, 138.0, 132.6, 122.8, 121.9, 120.3, 109.3, 82.9, 33.1, 25.0; $^{11}B\{^1H\}$ NMR (160 MHz, $CDCl_3$): δ 29.7.

Borylation of 3,4-ethylenedioxythiophene

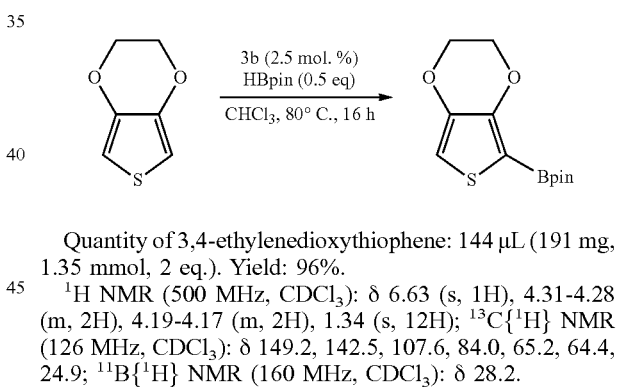

Quantity of 3,4-ethylenedioxythiophene: 144 μL (191 mg, 1.35 mmol, 2 eq.). Yield: 96%.

$^1$H NMR (500 MHz, $CDCl_3$): δ 6.63 (s, 1H), 4.31-4.28 (m, 2H), 4.19-4.17 (m, 2H), 1.34 (s, 12H); $^{13}C\{^1H\}$ NMR (126 MHz, $CDCl_3$): δ 149.2, 142.5, 107.6, 84.0, 65.2, 64.4, 24.9; $^{11}B\{^1H\}$ NMR (160 MHz, $CDCl_3$): δ 28.2.

Borylation of 2-tertbutylfuran

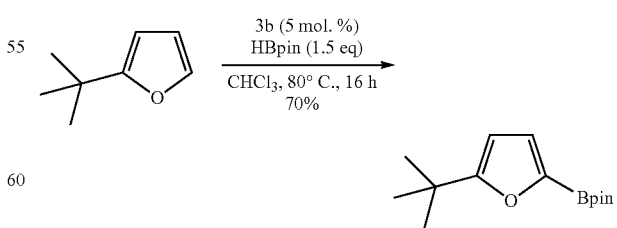

Quantity of 2-tertbutylfuran: 96 μL (83 mg, 0.67 mmol, limiting reagent); Quantity of HBPin: 161 μL (142 mg, 1.11 mmol, 1.5 eq.+15 mmol. % for deprotection). Yield: 112 mg (70%).

$^{1}$H NMR (500 MHz, CDCl$_3$): δ 6.98 (d, J=3.3 Hz, 1H), 6.02 (d, J=3.3 Hz, 1H), 1.33 (s, 12H), 1.31 (s, 9H); $^{13}$C{$^{1}$H} NMR (101 MHz, CDCl$_3$): δ 169.9, 124.8, 103.3, 84.0, 77.2, 33.1, 29.3, 24.9; $^{11}$B{$^{1}$H} NMR (160 MHz, CDCl$_3$): δ 27.4.

Borylation of 2-(trimethylsiloxy)furan

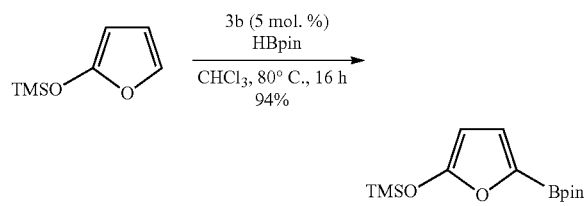

Quantity of 2-(trimethylsiloxy)furan: 229 μL (213 mg, 1.35 mmol, 2 eq.). Yield: 179 mg (94%). Although the product could be isolated, it tends to decompose under ambient conditions.

$^{1}$H NMR (400 MHz, CDCl$_3$): δ 6.96 (d, J=3.3, 1H), 5.18 (d, J=3.3, 1H), 1.31 (s, 12H), 0.30 (s, 9H); $^{13}$C{$^{1}$H} NMR (101 MHz, CDCl$_3$): δ 126.4, 110.2, 85.5, 83.9, 24.9, −0.1; $^{11}$B{$^{1}$H} NMR (160 MHz, CDCl$_3$): δ 26.7.

General procedure for gram scale catalytic borylation of heteroaromatic substrates in accordance with various embodiments of the present disclosure.

Borylation of 1-methylpyrrole

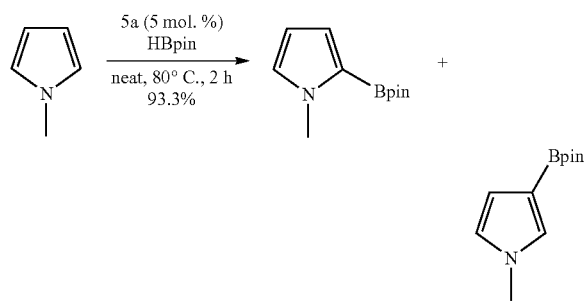

Precatalyst 5a (133 mg, 0.58 mmol) was introduced into an oven-dried two-neck flask (100 mL) containing a magnetic stirring bar and connected to a condenser that is already connected to a nitrogen flow line. N-methylpyrrole (1.1 mL, 11.6 mmol) followed by pinacolborane (1.15 eq., 2.1 mL) were then added via syringe. The reaction mixture was subsequently stirred for 10 min at room temperature and then for 2 hours in an oil bath kept at 80° C. The resulting mixture was kept under vacuum during 30 min, and then filtered through a short pad of Celite which was subsequently rinsed with ethyl ether. The resulting filtrate was evaporated to complete dryness under vacuum to afford 2.37 g (93.3%) of the desired product as a white solid composed of a 98:2 mixture of 1-methyl-2-(4,4,5,5-tetramethyl-1,3,2-dioxaborolan-2-yl)pyrrole and 1-methyl-3-(4,4,5,5-tetramethyl-1,3,2-dioxaborolan-2-yl)pyrrole.

Borylation of 1-methylindole

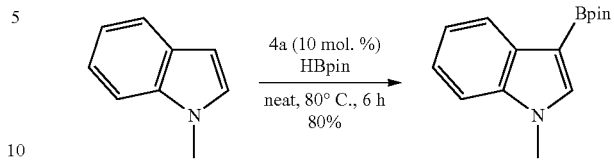

Precatalyst 4a (234 mg, 1.02 mmol) was introduced into an oven-dried two-neck flask (100 mL) containing a magnetic stirring bar and connected to a condenser that is already connected to a nitrogen flow line. N-methylindole (1.3 mL, 10.2 mmol) followed by pinacolborane (2.0 eq., 3.0 mL) were then added via syringe. The reaction mixture was subsequently stirred for 10 min at room temperature and then for 6 hours in an oil bath kept at 80° C. The resulting mixture was kept under vacuum during 30 min. The crude product was purified by flash column chromatography using silica gel as the stationary phase and a mixture of petroleum ether:ethyl ether (20:1) as the eluent to eliminate any unreacted N-methylindole. The eluent composition was then changed to a mixture of petroleum ether:ethyl ether (10:1) to afford the purified borylated product as a white solid (2.01 g; 80%).

Crystallographic Details

Crystals were mounted on CryoLoops with Paratone-N and optically aligned on a Bruker SMART APEX-II X-ray diffractometer with a 1K CCD detector using a digital camera. Initial intensity measurements were performed using a fine-focused sealed tube, graphite-monochromated, X-ray source (Mo Kα, λ=0.71073 Å) at 50 kV and 30 mA. Standard APEX-II software package was used for determining the unit cells, generating the data collection strategy, and controlling data collection. SAINT was used for data integration including Lorentz and polarization corrections. Semi-empirical absorption corrections were applied using SCALE (SADABS). The structures of all compounds were solved by direct methods and refined by full-matrix least-squares methods with SHELX-97 in the SHELXTL6.14 package. All of the H atoms on C atoms were generated geometrically and refined in riding mode.

Computational Details

All calculations were performed on the full structures of the reported compounds. Calculations were performed with the GAUSSIAN 09 suite of programs. The ωB97XD functional was used in combination with the 6-31G basis set for all atoms. The transition states were located and confirmed by frequency calculations (single imaginary frequency). The stationary points were characterized as minima by full vibration frequency calculations (no imaginary frequency). All geometry optimizations were carried out without any symmetry constraints. The energies were then refined by single point calculations to include solvent effects using the SMD solvation model with the experimental solvent, chloroform, at the ωB97XD/6-31+G level of theory.

Thermodynamics of the Formation of 3a-c

Molecular modeling was performed to rationalize the observations made while preparing precatalysts 3a-c. Indeed, as mentioned hereinabove, the formation of trifluoroborate salt 3a is favored in the case of long reaction times and/or high temperatures (thermodynamic product). By contrast, 3b and 3c are kinetic products that are formed initially in the reaction mixture. Calculations indicate that, after the hypothetic formation of a phenylene-bridged TMP-BF$_2$ FLP, the binding of HF by the latter is much more exergonic than that of H$_2$O and MeOH (Table 3). This supports the observation that 3a is thermodynamically downhill with regards to 3b-c.

TABLE 3

Computed binding energies of small molecules by a TMP-BF$_2$ FLP.

| Species | ΔH (kcal/mol) | ΔG (kcal/mol) |
| --- | --- | --- |
| TMPBF2 | 0 | 0 |
| TMPBF2 + MeOH (3b) | −31.42 | −18.35 |
| TMPBF2 + H$_2$O (3c) | −27.96 | −17.36 |
| TMPBF2 + HF (3a) | −36.13 | −26.48 |

While the present disclosure has been described with reference to specific examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

REFERENCES

1. Rousseaux, S.; Liégault, B.; Fagnou, K. In *Modern Tools for the Synthesis of Complex Bioactive Molecules*; Cossy, J., Arseniyadis, S., Eds.; John Wiley & Sons, Inc.: Hoboken, N.J., USA, 2012; pp 1-32.
2. Wencel-Delord, J.; Glorius, F. *Nat. Chem.* 2013, 5, 369-375.
3. Usluer, Ö.; Abbas, M.; Wantz, G.; Vignau, L.; Hirsch, L.; Grana, E.; Brochon, C.; Cloutet, E.; Hadziioannou, G. *ACS Macro Lett.* 2014, 3, 1134-1138.
4. Mkhalid, I. A. I.; Barnard, J. H.; Marder, T. B.; Murphy, J. M.; Hartwig, J. F. *Chem. Rev.* 2010, 110, 890-931.
5. Cho, J.-Y.; Tse, M. K.; Holmes, D.; Maleczka, R. E.; Smith, M. R. *Science* 2002, 295, 305-308.
6. Ishiyama, T.; Takagi, J.; Ishida, K.; Miyaura, N.; Anastasi, N. R.; Hartwig, J. F. *J. Am. Chem. Soc.* 2002, 124, 390-391.
7. Hall, D. G. *Boronic Acids*, 2nd Ed.; Wiley-VCH: Weinhein, 2011.
8. Miyaura, N.; Suzuki, A. *Chem. Rev.* 1995, 95, 2457-2483.
9. Chan, D. M.; Monaco, K. L.; Wang, R.-P.; Winters, M. P. *Tetrahedron Lett.* 1998, 39, 2933-2936.
10. Ishiyama, T.; Nobuta, Y.; Hartwig, J. F.; Miyaura, N. *Chem. Commun.* 2003, 2924.
11. Ishiyama, T.; Takagi, J.; Hartwig, J. F.; Miyaura, N. *Angew. Chem. Int. Ed. Engl.* 2002, 41, 3056-3058.
12. Tajuddin, H.; Harrisson, P.; Bitterlich, B.; Collings, J. C.; Sim, N.; Batsanov, A. S.; Cheung, M. S.; Kawamorita, S.; Maxwell, A. S.; Maxwell, A. C.; Shukla, L.; Morris, J.; Lin, Z.; Marder, T. B.; Steel, P. G. *Chem. Sci.* 2012, 3, 3505-3515.
13. Larsen, M. A.; Hartwig, J. F. *J. Am. Chem. Soc.* 2014, 136, 4287-4299.
14. International Conference on Harmonisation of Technical Requirements for Regitration of Pharmaceuticals for Human Use—Q3D Elemental Impurities http://www.fda.gov/downloads/drugs/guidancecomplianceregulatoryinformation/guidances/ucm371025.pdf). (accessed Jun. 20, 2015).
15. Mazzacano, T. J.; Mankad, N. P. *J. Am. Chem. Soc.* 2013, 135, 17258-17261.
16. Furukawa, T.; Tobisu, M.; Chatani, N. *Chem. Commun.* 2015, 51, 6508-6511.
17. Dombray, T.; Werncke, C. G.; Jiang, S.; Grellier, M.; Vendier, L.; Bontemps, S.; Sortais, J.-B.; Sabo-Etienne, S.; Darcel, C. *J. Am. Chem. Soc.* 2015, 137, 4062-4065.
18. Obligacion, J. V; Semproni, S. P.; Chirik, P. J. *J. Am. Chem. Soc.* 2014, 136, 4133-4136.
19. Hatanaka, T.; Ohki, Y.; Tatsumi, K. *Chem. Asian J.* 2010, 5, 1657-1666.
20. Prokofjevs, A.; Kampf, J. W.; Vedejs, E. *Angew. Chem. Int. Ed.* 2011, 50, 2098-2101.
21. Del Grosso, A.; Singleton, P. J.; Muryn, C. A.; Ingleson, M. J. *Angew. Chem. Int. Ed.* 2011, 50, 2102-2106.
22. Bagutski, V.; Del Grosso, A.; Carrillo, J. A.; Cade, I. A.; Helm, M. D.; Lawson, J. R.; Singleton, P. J.; Solomon, S. A.; Marcelli, T.; Ingleson, M. J. *J. Am. Chem. Soc.* 2013, 135, 474-487.
23. Stahl, T.; Müther, K.; Ohki, Y.; Tatsumi, K.; Oestreich, M. *J. Am. Chem. Soc.* 2013, 135, 10978-10981.
24. Del Grosso, A.; Pritchard, R. G.; Muryn, C. A.; Ingleson, M. *J. Organometallics* 2010, 29, 241-249.
25. Welch, G. C.; San Juan, R. R.; Masuda, J. D.; Stephan, D. W. *Science* 2006, 314, 1124-1126.
26. Stephan, D. W.; Erker, G. *Angew. Chem. Int. Ed.* 2010, 49, 46-76.
27. Stephan, D. W. *Acc. Chem. Res.* 2015, 48, 306-316.
28. Stephan, D. W.; Erker, G. *Angew. Chemie* Int. Ed. 2015, 54, 6400-6441.
29. Courtemanche, M.-A.; Pulis, A. P.; Rochette, É.; Légaré, M.-A.; Stephan, D. W.; Fontaine, F.-G. F.-G. *Chem. Commun.* 2015, 51, 9797-9800.
30. Greb, L.; Ofia-Burgos, P.; Schirmer, B.; Grimme, S.; Stephan, D. W.; Paradies, J. *Angew. Chem. Int. Ed. Engl.* 2012, 51, 10164-10168.
31. Mahdi, T.; Stephan, D. W. *J. Am. Chem. Soc.* 2014, 136, 15809-15812.
32. Stephan, D. W.; Erker, G. In *Frustrated Lewis Pairs I*; Stephan, D. W., Erker, G., Eds.; Springer: Berlin, Heidelberg, 2013; Vol. 332, pp 85-110.
33. Stephan, D. W. *Org. Biomol. Chem.* 2012, 10, 5740-5746.
34. Chase, P. A.; Welch, G. C.; Jurca, T.; Stephan, D. W. *Angew. Chem. Int. Ed.* 2007, 46, 8050-8053.
35. Hounjet, L. J.; Bannwarth, C.; Garon, C. N.; Caputo, C. B.; Grimme, S.; Stephan, D. W. *Angew. Chem. Int. Ed.* 2013, 52, 7492-7495.
36. Spies, P.; Schwendemann, S.; Lange, S.; Kehr, G.; Frohlich, R.; Erker, G. *Angew. Chem. Int. Ed.* 2008, 47, 7543-7546.
37. Chernichenko, K.; Madarisz, A.; Pipai, I.; Nieger, M.; Leskeli, M.; Repo, T. *Nat. Chem.* 2013, 5, 718-723.
38. Courtemanche, M.-A.; Larouche, J.; Légaré, M.-A.; Bi, W.; Maron, L.; Fontaine, F.-G. *Organometallics* 2013, 32, 6804-6811.
39. Courtemanche, M.-A.; Légaré, M.-A.; Maron, L.; Fontaine, F.-G. *J. Am. Chem. Soc.* 2013, 135, 9326-9329.
40. Courtemanche, M.-A.; Légaré, M.-A.; Maron, L.; Fontaine, F.-G. *J. Am. Chem. Soc.* 2014, 136, 10708-10717.
41. Das Neves Gomes, C.; Blondiaux, E.; Thudry, P.; Cantat, T. *Chem. Eur. J.* 2014, 20, 7098-7106.

42. Declercq, R.; Bouhadir, G.; Bourissou, D.; Légaré, M.-A.; Courtemanche, M.-A.; Nahi, K. S.; Bouchard, N.; Fontaine, F.-G.; Maron, L. *ACS Catal.* 2015, 5, 2513-2520.
43. Wang, T.; Stephan, D. W. *Chem. Eur. J.* 2014, 20, 3036-3039.
44. Wang, T.; Stephan, D. W. *Chem. Commun.* 2014, 50, 7007-7010.
45. Berkefeld, A.; Piers, W. E.; Parvez, M. *J. Am. Chem. Soc.* 2010, 132, 10660-10661.
46. Houghton, A. Y.; Hurmalainen, J.; Mansikkamäki, A.; Piers, W. E.; Tuononen, H. M. *Nat. Chem.* 2014, 6, 983-988.
47. Chernichenko, K.; Kótai, B.; Papai, I.; Zhivonitko, V.; Nieger, M.; Leskelai, M.; Repo, T. *Angew. Chem. Int. Ed.* 2015, 54, 1749-1753.
48. Legare, M.-A.; Courtemanche, M.-A.; Rochette, E.; Fontaine, F.-G. *Science* 2015, 349, 513-516.
49. Lafrance, M.; Fagnou, K. *J. Am. Chem. Soc.* 2006, 128, 16496-16497.
50. Vanchura, B. A.; Preshlock, S. M.; Roosen, P. C.; Kallepalli, V. A.; Staples, R. J.; Maleczka, R. E.; Singleton, D. A.; Smith, M. R. *Chem. Commun.* 2010, 46, 7724-7726.
51. Sather, A. C.; Lee, H. G.; Colombe, J. R.; Zhang, A.; Buchwald, S. L. *Nature* 2015, 524, 208-211.
52. Chernichenko, K.; Nieger, M.; Leskela, M.; Repo, T. *Dalt. Trans.* 2012, 41, 9029-9032.

The invention claimed is:

1. A precatalyst for the functionalization of a sp²-carbon, the precatalyst having the structure defined by Formula I:

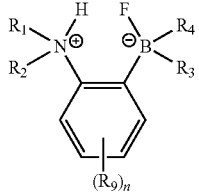

Formula I wherein:
R₁ and R₂ are independently, $C_{1-15}$alkyl, $C_{3-15}$branched alkyl, $C_{6-18}$aryl, $C_{6-18}$aryl having at least one $C_{1-10}$alkyl substituent, $C_{5-8}$cycloalkyl; $C_{5-8}$cycloalkyl having at least one $C_{1-10}$alkyl substituent; or
R₁ and R₂ are linked together to form a nitrogen containing ring system, wherein the nitrogen containing ring system is optionally substituted by one or more $C_{1-10}$alkyl groups;
R₃ and R₄ are independently hydrogen, halogen, $C_{1-15}$alkyl, $C_{3-15}$branched alkyl, $C_{6-18}$aryl, $C_{6-18}$aryl having at least one $C_{1-10}$alkyl substituent, $C_{5-8}$cycloalkyl; $C_{5-8}$cycloalkyl having at least one $C_{1-10}$alkyl substituent, $OR_5$, $SR_6$; or
R₃ and R₄ are linked together to form a boron containing ring system, wherein the boron containing ring system is optionally substituted by one or more $C_{1-10}$alkyl groups;
R₅ and R₆ are independently hydrogen, $C_{1-15}$alkyl or $C_{3-15}$branched alkyl;
R₉ is hydrogen, halogen, $C_{1-15}$alkyl, $C_{3-15}$branched alkyl, aryl, $OCF_3$, $CF_3$, $OR_5$ or $SR_6$;

wherein when R₉ is present more than once, each R₉ is independently hydrogen, halogen, $C_{1-15}$alkyl, $C_{3-15}$branched alkyl, aryl, $OCF_3$, $CF_3$, $OR_5$ or $SR_6$; and
n is an integer ranging from 1 to 4.

2. The precatalyst of claim 1,
wherein:
R₁ and R₂ are linked together to form a morpholine, piperazine, N'-alkyl piperazine, or thiomorpholine ring system that is optionally substituted by one or more $C_{1-10}$alkyl groups.

3. The precatalyst of claim 1, having a structure defined by Formula II:

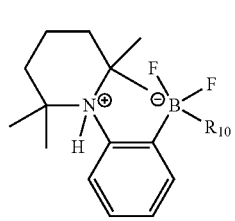

Formula II wherein:
R₁₀ is F or $OR_{11}$; and
R₁₁ is H, $C_{1-15}$alkyl or $C_{3-15}$branched alkyl.

4. The precatalyst of claim 3, having the Formula:

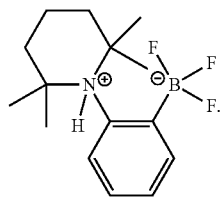 [SMILES: CC1(C)CCCC(C)(C)[NH+]1c1ccccc1[B-](F)(F)F]

5. The precatalyst of claim 3, having the Formula:

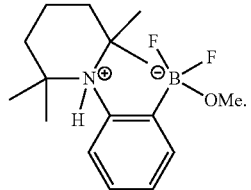 [SMILES: CO[B-](F)(F)c1ccccc1[NH+]1C(C)(C)CCCC1(C)C]

6. The precatalyst of claim 3, having the Formula:

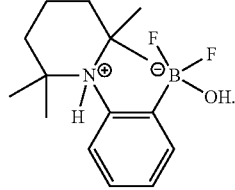 [SMILES: CC1(C)CCCC(C)(C)[NH+]1c1ccccc1[B-](O)(F)F]

7. The precatalyst of claim 1, having the Formula:

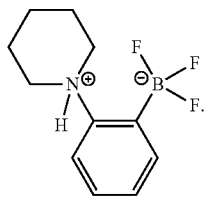 [SMILES: F[B-](F)(F)c1ccccc1[NH+]1CCCCC1]

8. The precatalyst of claim 1, having the Formula:

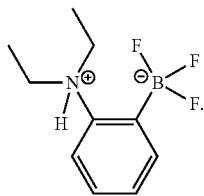

9. The precatalyst of claim 1, having the Formula:

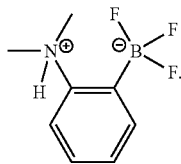

10. The precatalyst of claim 1, having a structure defined by Formula III:

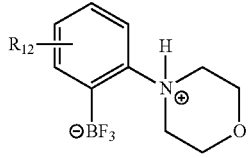

Formula III wherein $R_{12}$ is H, halogen, $C_{1-15}$alkyl, $C_{3-15}$branched alkyl, aryl, $OCF_3$, $CF_3$, $OR_5$ or $SR_6$; and $R_5$ and $R_6$ are independently hydrogen, $C_{1-15}$alkyl or $C_{3-15}$branched alkyl.

11. The precatalyst of claim 10, having the Formula:

12. A catalytic process for the functionalization of a $sp^2$ carbon, the process comprising:

contacting a precatalyst as defined in claim 1; a functionalization reagent; and a substrate comprising a $sp^2$—H carbon, under conditions to provide a substrate comprising a functionalized $sp^2$ carbon.

13. The catalytic process of claim 12, wherein the substrate is an alkene, an arene or a heteroarene.

14. The catalytic process of claim 12, wherein the functionalization reagent is an organoborane reagent.

15. The catalytic process of claim 14, wherein the organoborane reagent is HBPin, HBCat or 9BBN.

16. The catalytic process of claim 12, wherein the precatalyst is present from about 1 mol % to about 20 mol %.

17. A catalytic process for the dehydrogenative functionalization of a $sp^2$ carbon, the process comprising:

contacting a precatalyst as defined in claim 1; a functionalization reagent; and a substrate comprising a $sp^2$—H carbon, under conditions to provide a substrate comprising a functionalized $sp^2$ carbon.

18. The catalytic process of claim 17, wherein the substrate is an alkene, an arene or a heteroarene.

19. The catalytic process of claim 17, wherein the functionalization reagent is an organoborane reagent.

20. The catalytic process of claim 19, wherein the organoborane reagent is HBPin, HBCat or 9BBN.

21. The catalytic process of claim 17, wherein the precatalyst is present from about 1 mol % to about 20 mol %.

* * * * *